US008372880B2

(12) United States Patent
Gazit et al.

(10) Patent No.: US 8,372,880 B2
(45) Date of Patent: Feb. 12, 2013

(54) COMPOSITIONS AND METHODS USING SAME FOR TREATING AMYLOID-ASSOCIATED DISEASES

(75) Inventors: Ehud Gazit, Ramat-HaSharon (IL); Yair Porat, Hofit (IL)

(73) Assignee: Tel Aviv University Future Technology Development L.P., Tel Aviv (IL)

( * ) Notice: Subject to any disclaimer, the term of this patent is extended or adjusted under 35 U.S.C. 154(b) by 1128 days.

(21) Appl. No.: 11/386,880

(22) Filed: Mar. 23, 2006

(65) Prior Publication Data
US 2006/0194777 A1 Aug. 31, 2006

Related U.S. Application Data

(63) Continuation-in-part of application No. PCT/IL2004/000890, filed on Sep. 23, 2004.

(60) Provisional application No. 60/505,425, filed on Sep. 25, 2003, provisional application No. 60/553,953, filed on Mar. 18, 2004, provisional application No. 60/588,362, filed on Jul. 16, 2004.

(51) Int. Cl.
| A01N 43/26 | (2006.01) |
| A01N 43/12 | (2006.01) |
| A61K 31/385 | (2006.01) |
| A61K 31/38 | (2006.01) |
| C07D 327/04 | (2006.01) |
| C07D 343/00 | (2006.01) |
| C07D 327/10 | (2006.01) |
| C07D 339/02 | (2006.01) |
| C07D 341/00 | (2006.01) |
| C07D 409/00 | (2006.01) |
| C07D 411/00 | (2006.01) |
| C07D 495/00 | (2006.01) |
| C07D 497/00 | (2006.01) |

(52) U.S. Cl. ............... 514/439; 514/433; 549/33
(58) Field of Classification Search ............... 514/442, 514/470, 439, 443; 549/33, 466
See application file for complete search history.

(56) References Cited

U.S. PATENT DOCUMENTS

| 3,042,685 A | 3/1962 | Roussel |
| 2,920,080 A | 5/1965 | Bucourt et al. |
| 3,625,973 A | 12/1971 | Julia |
| 3,790,596 A | 2/1974 | Shkilkova et al. |
| 3,853,987 A | 12/1974 | Dreyer |
| 3,935,074 A | 1/1976 | Rubenstein et al. |
| 3,976,639 A | 8/1976 | Batcho et al. |
| 3,984,533 A | 10/1976 | Uzgiris |
| 4,036,945 A | 7/1977 | Haber |
| 4,299,917 A | 11/1981 | Berger et al. |
| 4,331,647 A | 5/1982 | Goldenberg |
| 4,626,540 A | 12/1986 | Capps et al. |
| 4,925,673 A | 5/1990 | Steiner et al. |
| 4,946,778 A | 8/1990 | Ladner et al. |
| 4,970,233 A | 11/1990 | McHugh |
| 5,013,556 A | 5/1991 | Woodle et al. |
| 5,155,107 A * | 10/1992 | Panzeri et al. ............ 514/232.8 |
| 5,210,215 A | 5/1993 | Politi et al. |
| 5,270,163 A | 12/1993 | Gold et al. |
| 5,304,470 A | 4/1994 | Fischer et al. |
| 5,332,648 A | 7/1994 | Kihara et al. |
| 5,475,096 A | 12/1995 | Gold et al. |
| 5,545,806 A | 8/1996 | Lonberg et al. |
| 5,545,807 A | 8/1996 | Surani et al. |
| 5,556,744 A | 9/1996 | Weiner et al. |
| 5,561,110 A * | 10/1996 | Michaelis et al. ............ 514/13 |
| 5,567,588 A | 10/1996 | Gold et al. |
| 5,569,825 A | 10/1996 | Lonberg et al. |
| 5,595,877 A | 1/1997 | Gold et al. |
| 5,625,126 A | 4/1997 | Lonberg et al. |
| 5,633,425 A | 5/1997 | Lonberg et al. |
| 5,637,459 A | 6/1997 | Burke et al. |
| 5,643,768 A | 7/1997 | Kawasaki |
| 5,658,754 A | 8/1997 | Kawasaki |
| 5,659,041 A | 8/1997 | Pollak et al. |
| 5,661,016 A | 8/1997 | Lonberg et al. |
| 5,683,867 A | 11/1997 | Biesecker et al. |
| 5,705,337 A | 1/1998 | Gold et al. |
| 5,916,642 A | 6/1999 | Chang |
| 6,162,828 A | 12/2000 | Fukuda et al. |
| 6,251,625 B1 | 6/2001 | Bommarius et al. |
| 6,255,286 B1 | 7/2001 | Yanai et al. |
| 6,261,569 B1 | 7/2001 | Comis et al. |
| 6,303,567 B1 | 10/2001 | Findeis et al. |
| 6,309,669 B1 | 10/2001 | Setterstrom et al. |
| 6,326,174 B1 | 12/2001 | Joyce et al. |
| 6,359,112 B2 | 3/2002 | Kapurniotu et al. |
| 6,361,861 B2 | 3/2002 | Gao et al. |
| 6,472,436 B1 * | 10/2002 | Schubert et al. ............ 514/731 |
| 6,593,339 B1 | 7/2003 | Eek et al. |
| 6,610,478 B1 | 8/2003 | Takle et al. |
| 6,613,875 B1 | 9/2003 | Ghadiri |
| 6,617,114 B1 | 9/2003 | Fowlkes et al. |
| 6,677,153 B2 | 1/2004 | Iversen |
| 6,689,753 B1 | 2/2004 | Soto-Jara |
| 6,858,318 B2 | 2/2005 | Kogiso et al. |
| 6,976,639 B2 | 12/2005 | Williams et al. |
| 7,045,537 B1 | 5/2006 | Woolfson et al. |

(Continued)

FOREIGN PATENT DOCUMENTS

| DE | 3412445 | 10/1985 |
| DE | 10043282 | 3/2002 |

(Continued)

OTHER PUBLICATIONS

Patani et. al. Chem. Rev., 1996, American Chemical Society, vol. 96, 3147-3176.*

(Continued)

Primary Examiner — Sreeni Padmanabhan
Assistant Examiner — Sarah Pihonak

(57) ABSTRACT

Compounds having one or more phenol moieties, derivatives thereof, compositions containing same and uses thereof for the treatment of amyloid-associated diseases are provided.

2 Claims, 21 Drawing Sheets
(18 of 21 Drawing Sheet(s) Filed in Color)

U.S. PATENT DOCUMENTS

| | | |
|---|---|---|
| 2001/0041732 A1 | 11/2001 | Gurley et al. |
| 2002/0006954 A1 | 1/2002 | Hensley et al. |
| 2002/0086067 A1 | 7/2002 | Choi et al. |
| 2002/0151506 A1 | 10/2002 | Castillo et al. |
| 2003/0130484 A1 | 7/2003 | Gordon et al. |
| 2003/0158237 A1 | 8/2003 | Saragovi et al. |
| 2003/0225155 A1 | 12/2003 | Fernandez-Pol et al. |
| 2004/0029830 A1 | 2/2004 | Herbert |
| 2004/0152672 A1 | 8/2004 | Carson et al. |
| 2005/0069950 A1 | 3/2005 | Haynie |
| 2006/0079454 A1 | 4/2006 | Reches et al. |
| 2006/0079455 A1 | 4/2006 | Gazit et al. |
| 2006/0089380 A1 | 4/2006 | Barnham et al. |
| 2006/0234947 A1 | 10/2006 | Gazit |
| 2007/0021345 A1 | 1/2007 | Gazit |
| 2007/0135334 A1 | 6/2007 | Gazit |
| 2007/0298043 A1 | 12/2007 | Gazit et al. |
| 2008/0305040 A1 | 12/2008 | Klunk |

FOREIGN PATENT DOCUMENTS

| | | |
|---|---|---|
| EP | 0081122 | 6/1983 |
| EP | 0421946 | 4/1991 |
| EP | 0885904 | 3/2004 |
| EP | 966975 | 7/2005 |
| JP | 59-044313 | 3/1984 |
| JP | 60-040061 | 2/1985 |
| JP | 63-044895 | 2/1988 |
| JP | 63-275579 | 11/1988 |
| JP | 02-295923 | 6/1990 |
| JP | 07017964 * | 1/1995 |
| JP | 10-245342 | 9/1998 |
| JP | 2000-193661 | 7/2000 |
| JP | 2003-519192 | 6/2003 |
| WO | WO 80/00789 | 1/1980 |
| WO | WO 92/19253 | 11/1992 |
| WO | WO 95/08999 | 4/1995 |
| WO | WO 96/28471 | 9/1996 |
| WO | WO 97/16191 | 9/1997 |
| WO | WO 98/20135 | 5/1998 |
| WO | WO9922728 * | 5/1999 |
| WO | WO 99/42102 | 8/1999 |
| WO | WO 99/58652 | 11/1999 |
| WO | WO 00/24390 | 4/2000 |
| WO | WO 01/05421 | 1/2001 |
| WO | WO 01/10457 | 2/2001 |
| WO | WO 01/21188 | 3/2001 |
| WO | WO 01/34631 | 5/2001 |
| WO | WO 01/45726 | 6/2001 |
| WO | WO 01/49281 | 7/2001 |
| WO | WO 01/49307 | 7/2001 |
| WO | WO 01/93836 | 12/2001 |
| WO | WO 02/072086 | 9/2002 |
| WO | WO 02/094857 | 11/2002 |
| WO | WO 03/013442 | 2/2003 |
| WO | WO 03/024443 | 3/2003 |
| WO | WO 03/032969 | 4/2003 |
| WO | WO 03/032969 A2 * | 4/2003 |
| WO | WO 03/039540 | 5/2003 |
| WO | WO 03/063760 | 7/2003 |
| WO | WO 03/070269 | 8/2003 |
| WO | WO 03/077866 | 9/2003 |
| WO | WO 03105838 A2 * | 12/2003 |
| WO | WO 2004/052773 | 6/2004 |
| WO | WO 2004/060791 | 7/2004 |
| WO | WO 2005/016339 | 2/2005 |
| WO | WO 2005/020809 | 3/2005 |
| WO | WO 2005/027901 | 3/2005 |
| WO | WO 2005/031362 | 4/2005 |
| WO | WO 2005/085867 | 9/2005 |
| WO | WO 2006/006172 | 1/2006 |
| WO | WO 2006/018850 | 2/2006 |
| WO | WO 2006/020681 | 2/2006 |
| WO | WO 2006/027780 | 3/2006 |
| WO | WO 2006/013552 | 9/2006 |
| WO | WO 2007/029003 | 3/2007 |
| WO | WO 2007/043048 | 4/2007 |

OTHER PUBLICATIONS

Amidon et. al., Transport Processes in Pharmaceutical Systems, 2000, Dekker, vol. 102, p. 186.*

Reddy et. al., Neurotoxicity Research, 2002, Taylor & Francis Ltd., vol. 4, issue 3, pp. 191-209.*

Sacchettini et. al., Nature Reviews, 2002, Nature Publishing Group, vol. 1, pp. 267-275.*

Michaelides et. al., Journal of Medicinal Chemistry, 1995, American Chemical Society, vol. 38, pp. 3445-3447.*

Song et. al., Bioorganic and Medicinal Chemistry Letters, 2003, Pergamon, vol. 13, pp. 297-300.*

Hoppener et. al., the New England Journal of Medicine, 2000, Massachusetts Medical Society, vol. 343, No. 6, pp. 411-419.*

Lazaris et al. "Spider Silk Fibers Spun From Soluble Recombinant Silk Produced in Mammalian Cells", Science, 295: 472-476, 2002. p. 474-475.

Gazit "Mechanisms of Amyloid Fibril Self-Assembly and Inhibition Model Short Peptides as a Key Research Tool", The FEBS Journal, 272: 5971-5978, 2005.

Jack et al. "The Organization of Aromatic Side Groups in an Amyloid Fibril Probed by Solid-State 2H and 19F NMR Spectroscopy", Journal of the American Chemical Society, JACS, 128: 8098-8099, 2006.

Reches et al. "Designed Aromatic Homo-Dipeptides: Formation of Ordered Nanostructures and Potential Nanotechnological Applications", Physical Biology, 3: S10-S19, 2006.

Mahler et al. "Rigid, Self-Assembled Hydrogel Composed of a Modified Aromatic Dipeptide", Advanced Materials, 18(11): 1365-1370, 2006.

Akazome et al. "Enantioselective Inclusion of Methyl Phenyl Sulfoxides and Benzyl Methyl Sulfoxides by (R)-Phenylglycyl-(R)-Phenylglycine and the Crystal Structures of the Inclusion Cavities", Journal of Organic Chemistry, 65(1): 68-76, 2000.

Anguiano et al. "Protofibrillar Islet Amyloid Polypeptide Permeabilizes Synthetic Vesicles by a Pore-Like Mechanism That May Be Relevant to Type II Diabetes", Biochemistry, 41: 11338-11343, 2002.

Arvinte et al. "The Structure and Mechanism of Formation of Human Calcitonin Fibrils", The Journal of Biological Chemistry, 268(9): 6415-6422, 1993.

Austin et al. "Medical Progress: Calcitonin. Physiology and Pathophysiology", The New England Journal of Medicine, 304(5): 269-278, 1981.

Balaram "De Novo Design: Backbone Conformational Constraints in Nucleating Helices and β-Hairpins", Journal of Peptide Research, 54: 195-199, 1999.

Balbach et al. "Supramolecular Structure in Full-Length Alzheimer's β-Amyloid Fibrils: Evidence for a Parallel β-Sheet Organization From Solid-State Nuclear Magnetic Resonance", Biophysical Journal, 83: 1205-1216, 2002.

Bauer et al. "Interfacial Adsorption and Aggregation Associated Changes in Secondary Structure of Human Calcitonin Monitored by ATR-FTIR Spectroscopy", Biochemistry, 33: 12276-12282, 1994.

Benvenga et al. "Homology of Calcitonin With the Amyloid-Related Proteins", Journal of Endocrinological Investigation, 17: 119-122, 1994.

Berger et al. "Calcitonin-Like Immunoreactivity of Amyloid Fibrils in Medullary Thyroid Carcinomas", Virchows Archiv A Pathological Anatomy and Histopathology, 412: 543-551, 1988.

Berson et al. "Proprotein Convertase Cleavage Liberates a Fibrillogenic Fragment of a Resident Glycoprotein to Initiate Melanosome Biogenesis", Journal of Cell Biology, 161(3): 521-533, 2003.

Bird et al. "Single-Chain Antigen-Binding Proteins", Science, 242(4877): 423-426, 1988.

Boerner et al. "Production of Antigen-Specific Human Monoclonal Antibodies From In Vitro-Primed Human Splenocytes", The Journal of Immunology, 147(1): 86-95, 1991.

Bong et al. "Self-Assembling Organic Nanotubes", Angewandte Chemie, International Edition, 40: 988-1011, 2001.

Chapman et al. "Role of *Escherichia coli* Curli Operons in Directing Amyloid Fiber Formation", Science, 295(5556): 851-855, 2002, Abstract.

Cherny et al. "The Formation of *Escherichia coli* Curli Amyloid Fibrils is Mediated by Prion-Like Peptide Repeats", Journal of Molecular Biology, 352(2): 245-252, 2005.

Cherny et al. "The YefM Antitoxin Defines a Family of Natively Unfolded Proteins", The Journal of Biological Chemistry, 279(9): 8252-8261, 2004.

Choplin "Computers and the Medicinal Chemist", Comprehensive Medicinal Chemistry, 4(Chap.17.2): 33-58, 1990.

Chou et al. "Conformational Parameters for Amino Acids in Helical, β-Sheet, and Random Coil Regions Calculated From Proteins", Biochemistry, 13(2): 211-222, 1974.

Chou et al. "Empirical Predictions of Protein Conformation", Annual Reviews in Biochemistry, 47: 251-276, 1978.

Claessen et al. "A Novel Class of Secreted Hydrophodic Proteins is Involved in Aerial Hyphae Formation in *Streptomyces coelicolor* by Forming Amyloid-Like Fibrils", Genes & Development, 17: 1714-1726, 2003.

Claessens et al. "Review Commentary: π-π Interactions in Self-Assembly", Journal of Physical Organic Chemistry, 10: 254-272, 1997.

Clark et al. "Self-Assembling Cyclic β3-Peptide Nanotubes as Artificial Transmembrane Ion Channels", Journal of the American Chemical Society, JACS, 120: 651-656, 1998.

Cole et al. "The EBV-Hybridoma Technique and Its Application to Human Lung Cancer", Monoclonal Antibodies and Cancer Therapy, Proceedings of the Roche- UCLA Symposium, Park City, Utah, p. 77-96, 1985.

Copp "Endocrine Regulation of Calcium Metabolism", Annual Reviews in Physiology, 32: 61-86, 1970.

Elliot et al. "The Chaplins: A Family of Hydrophobic Cell-Surface Proteins Involved in Aerial Mycelium Formation in *Streptomyces coelicolor*", Genes & Development, 17: 1727-1740, 2003.

Engelberg-Kulka et al. "Bacterial Programmed Cell Death Systems as Targets for Antibiotics", Trends in Microbiology, vol. 12 (2): p. 66-71, 2004.

Findeis et al. "Modified-Peptide Inhibitors of Amyloid β-Peptide Polymerization", Biochemistry, 38: 6791-6800, 1999.

Fingl et al. "Inroduction: General Principles", The Pharmacological Basis of Therapeutics, 5th Ed., Sec.I(Chap.1): 1-53, 1975.

Fishwild et al. "High-Avidity Hum IgGκ Monoclonal Antibodies From a Novel Strain of Minilocus Transgenic Mice", Nature Biotechnology, 14: 845-851, 1996.

Forloni et al. "Anti-Amyloidogenic Activity of Tetracyclines: Studies in Vitro", FEBS Letters, 487(3): 404-407, 2001. Figs. 1,3.

Gazit "Mechanistic Studies of Process of Amyloid Fibrils Formation by the Use of Peptide Fragments and Analogues: Implications for the Design of Fibrillization Inhibitors", Current Medicinal Chemistry, 9: 1725-1735, 2002.

Ghadiri et al. "Self-Assembling Organic Nanotubes Based on a Cyclic Peptide Architecture", Nature, 366: 324-327, Dec. 25, 1993.

Ghadiri et al. "Artificial Transmembrane Ion Channels From Self-Assembling Peptide Nanotubes", Nature, 369(6478): 301-304, 1994.

Gillard et al. "Controlling Self-Assembly", Chemical European Journal, 3(12): 1933-1940, 1997.

Görbitz "Nanotube Formation by Hydrophobic Dipeptides", Chemistry, 7(23): 5153-5159, 2001, Abstract.

Grady et al. "Axe—Txe, A Broad-Spectrum Proteic Toxin—Antitoxin System Encoded by a Multidrug-Resistant, Clinical Isolate of *Enterococcus faecium*", Molecular Microbiology, vol. 47(5: p. 1419-1432, 2003.

Häggqvist et al. "Medin: An Integral Fragment of Aortic Smooth Muscle Cell-Produced Lactadherin Forms the Most Common Human Amyloid", Proc. Natl. Acad. Sci. USA, 96: 8669-8674, 1999.

Haldar et al. "First Crystallographic Signature of the Highly Ordered Supramolecular Helical Assemblage From a Tripeptide Containing a Non-Coded Amino Acid", Tetrahedron Letters, 43(14): 2653-2656, 2002. Abstract.

Harlow et al. "Antibodies: A Laboratory Manual", Cold Spring Harbor Laboratory, p. III-IX, 1988.

Harrison et al. "Amyloid Peptides and Proteins in Review", Reviews in Physiology, Biochemistry and Pharmacology, 159: 1-77, 2007.

Hartgerink et al. "Peptide Nanotubes and Beyond", Chemistry European Journal, 4(8): 1367-1372, 1998. Abstract.

Holmes et al. "Extensive Neurite Outgrowth and Active Synapse Formation on Self-Assembling Peptide Scaffolds", Proc. Natl. Acad. Sci. USA, 97(12): 6728-6733, 2000.

Hoogenboom et al. "By-Passing Immunisation. Human Antibodies From Synthetic Repertoires of Germline $V_H$ Gene Segments Rearranged In Vitro", Journal of Molecular Biology, 227: 381-388, 1992.

Horne et al. "A Heterocyclic Peptide Nanotube", Journal of the American Chemical Society, JACS, 125(31): 9372-9376, Aug. 6, 2003. Abstract.

Hoyle et al. "*Pseudomonas aeruginosa* Biofilm as a Diffusion Barrier to Piperacillin", Antimicrobial Agents and Chemotherapy, 36(9): 2054-2056, 1992.

Huang et al. "A Review on Polymer Nanofibers by Electrospinning and Their Applications in Nanocomposites", Composites Science and Technology, 63: 2223-2253, 2003.

Inbar et al. "Localization of Antibody-Combining Sites Within the Variable Portions of Heavy and Light Chains", Proc. Natl. Acad. Sci. USA, 69(9): 2659-2662, 1972.

Jayawarna et al. "Nanostructured Hydrogels for Three-Dimensional Cell Culture Through Self-Assembly of Fluorenylmethoxycarbonyl-Dipeptides", Advanced Materials, 18: 611-614, 2006.

Jin "Electrospinning Bombyx Mori Silk With Poly (Ethylene Oxide)" Biomacromolecules, 3: 1233-1239, 2002.

Jones et al. "Replacing the Complementarity-Determining Regions in a Human Antibody With Those From a Mouse", Nature, 321: 522-525, 1986.

Kamihira et al. "Conformational Transitions and Fibrillation Mechanism of Human Calcitonin as Studied by High-Resolution Solid-State 13C NMR [in Process Citation]", Protein Science, 9: 867-877, 2000.

Kanaori et al. "Study of human Calcitonin Fibrillation by Proton Nuclear Magnetic Resonance Spectroscopy", Biochemistry, 34: 12138-12143, 1995.

Kaplan "Fibrous Proteins-Silk as a Model System", Polymer Degradation and Stability, 59: 25-32, 1998.

Kapurniotu et al. "Structure-Based Design and Study of Non-Amyloidogenic, Double N-Methylated IAPP Amyloid Core Sequences as Inhibitors of IAPP Amyloid Formation and Cytotoxicity", Journal of Molecular Biology, 315: 339-350, 2002.

Kedar et al. "In Vitro Synthesis of 'Amyloid' Fibrils From Insulin, Calcitonin and Parathormone", Israel Journal of Medical Science, 12(10): 1137-1140, 1976.

Kubik "High-Performance Fibers From Spider Silk", Angewandte Chemie, International Edition, 41(15): 2721-2723, 2002.

Kyte et al. "A Simple Method for Displaying the Hydropathic Character of a Protein", Journal of Molecular Biology, 157: 105-132, 1982.

Lansbury "Following Nature's Anti-Amyloid Strategy", Nature Biotechnology, 19(2): 112-113, 2001. p. 112, Left-Hand Col., Paragraph 1—Middle Col., Paragraph 1.

Larrick et al. "PCR Amplification of Antibody Genes", Methods: A Companion to Methods in Enzymology, 2(2): 106-110, 1991.

Lee et al. "Virus-Based Febrication of Micro- and Nanofibers Using Electrospinnig" Nano Letters,4(3): 387-390, 2004.

Liao et al. "Triphenylmethane Dyes as Inhibitors of Reverse Transcriptase RNA Polymerase and Protein Synthesis: Structure Activity Relationships", Journal of Medicinal Chemistry, 18(1): 117-120, 1975. Abstract.

Lonberg et al. "Antigen-Specific Human Antibodies From Mice Comprising Four Distinct Genetic Modifications", Nature, 368(6474): 856-859, 1994.

Lonberg et al. "Human Antibodies From Transgenic Mice" International Review of Immunology, 13: 65-93, 1995.

Lowe et al. "Structure-Function Relationships for Inhibitors of β-Amyloid Toxicity Containing the Recognition Sequence KLVFF", Biochemistry, 40: 7882-7889, 2001.

Lyon et al. "Self-Assembly and Gelation of Oxidized Gluthathione in Organic Solvents", Journal of the American Chemical Society, 123: 4408-4413, 2001.

Mah et al. "A Genetic Basis for *Pseudomonas aeruginosa* Biofilm Antibiotic Resistance", Nature, 426: 306-310, 2003.

Maji et al. "Fibril-Forming Model Synthetic Peptides Containing 3-Aminophenylacetic Acid", Tetrahedron, 58(43): 8695-8702, 2002, Abstract.

Marks et al. "By-Passing Immunization—Human Antibodies from V-Gene Libraries Displayed on Phage", Journal of Molecular Biology, 222: 581-597, 1991.

Marks et al. "By-Passing Immunization: Building High Affinity Human Antibodies by Chain Shuffling", Bio/Technology, 10: 779-783, 1992.

Matsui et al. "Crystalline Glyclylglycine Bolaamphiphile Tubules and Their pH-Sensitive Structural Transformation" The Journal of Physical Chemistry B, 104(15): 3384-3386, 2000.

Maury et al. "Creation of Amyloid Fibrils From Mutant ASN187 Gelsolin Peptides", Biochemical and Biophysical Research Communications, 183(1): 227- 231, 1992.

McGaughey et al. "π-Stacking Interactions", The Journal of Biological Chemistry, 273(25): 15458-15463, 1998.

Meluleni et al. "Mucoid *Pseudomonas aeruginosa* Growing in a Biofilm in Vitro are Killed by Opsonic Antibodies to the mucoid Exopolysaccharide Capsule but Not by Antibodies Produced During Chronic Lung Infection in Cystic Fibrosis Patients,", Journal of Immunology, 155: 2029-2038, 1995.

Morrison "Success in Specification", Nature, 368(6474): 812-813, 1994.

Mosmann "Rapid Colorimetric Assay for Cellular Growth and Survival: Application to Proliferation and Cytotoxicity Assays", Journal of Immunological Methods, 65: 55-63, 1983.

Mosselman et al. "The Complete Islet Amyloid Polypeptide Precursor is Encoded by Two Exons", FEBS Letters, 247: 154-158, 1989, Database Accession No. S04016.

Murphy et al. "Biofilm Formation by Nontypeable *Haemophilus influenzae*: Strain variability, Outer Membrane Antigen Expression and Role of pili", BMC Microbiology, 2(7): 1471-2180, 2002.

Mutter "Studies on the Coupling Rates in Liquid-Phase Peptide Synthesis Using Competition Experiments", International Journal of Peptide Protein Research, 13: 274-277, 1979.

Neuberger "Generating High-Avidity Human Mabs in Mice", Nature Biotechnology, 14: 826, 1996.

Nicolaus "Symbiotic Approach to Drug Design", Decision Making in Drug Research, p. 173-186, 1983.

Offen et al. "A Low Molecular Weight Copper Chelator Crosses the Blood-Brain Barrier and Attenuates Experimental Autoimmune Encephalomyelitis", Journal of Neurochemistry, 89: 1241-1251, 2004.

Pack et al. "Improved Bivalent Miniantibodies, With Identical Avidity as Whole Anitbodies, Produced by High Cell Density Fermentation of *Escherichia coli*", Bio/Technology, 11: 1271-1277, 1993.

Petkova et al. "A Structural Model for Alzheimer's β-Amyloid Fibrils Based on Experimental Constraints From Solid State NMR", Proc. Natl. Acad. Sci. USA, 99(26): 16742-16747, 2002.

Pettmann et al. "Morphological and Biochemical Maturation of Neurones Cultured in the Absence of Glial Cells", Nature, 281: 378-380, 1979.

Pispisa et al. "A Spectroscopic and Molecular Mechanics Investigation on A Series of AIB-Based Linear Peptides and A Peptide Template, Both Containing Tryptophan and A Nitroxide Derivative as Probes", Biopolymers, 53: 169-181, 2000.

Porter "The Hydrolysis of Rabbit γ-Globulin and Antibodies With Crystalline Papain", Biochemical Journal, 73: 119-126, 1959.

Presta "Antibody Engineering", Current Opinion in Structural Biology, 2: 593-596, 1992.

Puchtler et al. "A Review of Early Concepts of Amyloid in Context With Contemporary Chemical Literature From 1839 to 1859", The Journal of Histochemistry and Cytochemistry, 14(2): 123-134, 1966.

Reches et al. "Amyloid Fibril Formation by Pentapeptide and Tetrapeptide Fragments of Human Calcitonin", The Journal of Biological Chemistry, 277(38): 35475-35480, 2002.

Reches et al. "Casting Metal Nanowires Within Discrete Self-Assembled Peptide Nanotubes", Science, 300(5619): 625-627, 2003, Abstract.

Reches et al. "Self-Assembly of Peptide Nanotubes and Amylois-Like Structures by Charged-Termini-Capped Diphenylalanine Peptide Analogues", Israel Journal of Chemistry, 45(3): 363-371, 2005.

Reches et al. "Supporting Online Material", Science, 300(5619): 1-9, 2003. Retrieved From the Internet: URL:http://www.sciencemag.org/cgi/data/300/5619/625/DC1.

Riechmann et al. "Reshaping Human Antibodies for Therapy", Nature, 332: 323-329, 1988.

Sacchettini et al. "Therapeutic Strategies for Human Amyloid Diseases", Nature Reviews: Drug Discovery, 1: 267-275, 2002.

Shetty et al. "Aromatic π-Stacking in Solution as Revealed Through the Aggregation of Phenylacetylene Macrocycles", Journal of the American Chemical Society, 118: 1019-1027, 1996.

Sigel-Causey et al. "Phylogeny of the Pelecaniformes: Molecular Systematics of a Privative Group", Avian Molecular Evolution and Systematics, academic Press, p. 159-171, NBCI GenBank, Accession No. AAB58518, 1997.

Solomon et al. "Disaggregation of Alzheimer β-Amyloid by Site-Directed MAb", Proc. Natl. Acad. Sci. USA, 94: 4109-4112, 1997.

Stewart "Theoretical Aspects of Antibiotic Diffusion Into Microbial Biofilms", Antimicrobial Agents and Chemotherapy, 40(11): 2517-2522, 1996.

Sun et al. "Aromatic Van der Waals Clusters: Structure and Nonrigidity", Journal of Physical Chemistry, 100: 13348-13366, 1996.

Tjernberg et al. "Arrest of β-Amyloid Fibril Formation by a Pentapeptide Ligand", The Journal of Biological Chemistry, 271(15): 8545-8548, 1996.

Tjernberg et al. "Controlling Amyloid β-Peptide Fibril Formation With Protease-Stable Ligands", The Journal of Biological Chemistry, 272(19): 12601-12605, 1997.

Toledano et al. "Enzyme-Triggered Self-Assembly of Peptide Hydrogels Via Reversed Hydrolysis", Journal of the American Chemical Society, JACS, 128(4): 1070-1071, 2006.

Tonkinson et al. "Antisense Oligodeoxynucleotides as Clinical Therapeutic Agents", Cancer Investigation, 14(1): 54-65, 1996.

True et al. "Epigenetic Regulation of Trenslation Reveals Hidden Genetic Variation to Produce Complex Traits", Nature, 431: 184-187, 2004.

Tsai et al. "Synthesis of AIB-Containing Peptidomimetics as Potential Inhibitors of Alzheimer's γ-Secretase", 218th ACS National Meeting, New Orleans, USA, Meeting Abstract, MEDI-018, 1999. Abstract.

Tsang et al. "A Simple Chemical Method of Opening and Filling Carbon Nanotubes", Nature, 372: 159-162, 1994.

Tuite et al. "Propagation of Yeast Prions", Nature Reviews, 4: 878-889, 2003.

Vauthey et al. "Molecular Self-Assembly of Surfactant-Like Peptides to Form Nanotubes and Nanovesicles", Proc. Natl. Acad. Sci. USA, 99(8): 5355-5360, 2002.

Verhoeyen et al. "Reshaping Human Antibodies: Grafting an Antilysozyme Activity", Science, 239: 1534-1536, 1988.

Vidal et al. "A Stop-Codon Mutation in the BRI Gene Associated With Familial British Dementia", Nature, 399: 776-781, 1999.

Whitlow et al. "Single-Chain Fv Proteins and Their Fusion Proteins", Methods: A Companion to Methods in Enzymology, 2(2): 97-105, 1991.

Wolfenden et al. "Affinities of Amino Acid Side Chains for Solvent Water", Biochemistry, 20: 849-855, 1981.

Yokoi et al. "Dynamic Reassembly of Peptide RADA16 Nanofiber Scaffold", Proc. Natl. Acad. Sci. USA, 102(24): 8414-8419, 2005.

Zaidi et al. "Forty Years of Calcitonin—Where Are We Now? A Tribute to the Work of Iain Macintyre, FRS", Bone, 30(5): 655-663, 2002.

Zhang et al. "Supramolecular Hydrogels Respond to Ligand-Receptor Interaction", Journal of the American Chemical Society, 125(45): 13680-13681, 2003.

Nakajima "Amine Precursor Therapy: Manipulation of Brain Amine Activity With Precursor Amino Acid", Psychiatry and Clinical Neurosciences, 51(5), 267-274, 1997. p. 269, col. 1, § 2, 3.

Lee et al. "Anti-Diabetic Constituent From the Node of Lotus Rhizome (Nelumbo *Nucifera gaertn*)", Natural Product Sciences, 7(4), 107-109, 2001. p. 108, col. 1, Last §-col. 2, § 1.

Honma et al. "Use of a Thromboxane A2 Antagonist or Synthase Inhibitor for Treating Central Nervous System Diseases, e.g. Alzheimer Type Dementia." Database WPI, Section Ch. Week 200039, Derwent Publications, AN 2000-451668. & WO 00/30683 (Yagami et al.), Jun. 2, 2000. Abstract.

Losert et al. "Effect of Indole 3 Alkanecarboxylic Acifs on Glucose Utilization in Rats" Arzneimittel-Forschung/Drug Research, 25(6): 880-887, 1975. p. 880, col. 1, § 6, p. 886, col. 2, § 4, 5, p. 887, col. 1, § 3.

Kiselev "Pharmaceutical Composition for Prophylaxis and Treatment of Uterus Cervix Dysplasia and Cancer and Larynx Papillomatosis and Methods of Prophylaxis and Treatment of Said Sicknesses Based on Thereof", Database WPI, Section Ch, Week 200328, Derwent Publications, AN 2003-286683 & RU 2196568 C1 (Kiselev) Jan. 20, 2003. Abstract.

Kon-Ya et al "Indole Derivatives as Potent Inhibitors of Larval Settlement by the Barnacle, Balanus Amphitrite", Bioscience Biotechnology Biochemistry, JP, 58(12): 2178-2181, 1994. Compound 102.

Appukkuttan et al. "Microwave Enhanced Formation of Electron Rich Arylboronates", Synlett, 8: 1204-1206, 2003. Figs. Scheme 4, Compounds 5A, 5B, 5C, 5D.

Beugelmans Database Crossfire Beilstein [Online], Beilstein Institut zur Förderung der Chemischen Wissenschaften, Frankfurt am Main, DE, Database Accession No. 116671 (BRN) Compounds INDOL-2-YL-Methanol & Beugelmans R.: Bulletin de la Société Chimique Française, p. 335-336, 1969.

Cohen et al "Inhibition of Amyloid Fibril Formation and Cytotoxicity by Hydroxyindole Derivatives", Biochemistry, 45: 4727-4735, 2006. Abstract, p. 4728, col. 1, Last §, p. 4728, col. 2, § 2, Fig.1, p. 4729, col. 1, p. 4728, col. 1, Last §, p. 4728, col. 2, § 2, Fig.1, p. 4728, col. 1, Last §, p. 4728, col. 2, §2, Fig.1, 4, p. 4732, col. 2, § 2,3, p. 4733, col. 2, § 4

Altland et al. "Potential Treatment of Transthyretin-Type Amyloidoses by Sulfite", Neurogenetics, 2: 183-188, 1999.

Azriel et al. "Analysis of the Minimal Amyloid-Forming Fragment of the Islet Amyloid Polypeptide", The Journal of Biological Chemistry, 276(36): 34156-34161, 2001.

Kimura et al. "Analysis and Prediction of Absorption Profile Including Hepatic First-Pass Metabolism of N-Methyltyramine, A Potent Stimulant of Gastrin Release Present in Beer, After Oral Ingestion in Rats by Gastrointestinal-Transit-Absorption Model", Drug Metabolism and Disposition, 28(5): 577-581, 2000.

Higaki et al. "Regulation of Drug Absorption From Small Intestine by Enteric Nervous System I: A Poorly Absorbable Drug Via Passive Diffusion", Drug Metabolism and Pharmacokinetics, 19(3): 198-205, 2004.

Kisilevsky et al. "Arresting Amyloidosis In Vivo Using Small-Molecule Anionic Sulphonates or Sulphates: Implications for Alzheimer's Disease", Nature Medicine, 1: 143-148, 1995. Abstract.

Kocisko et al. "New Inhibitors of Scrabie-Associated Prion Protein Formation in a Library of 2,000 Drugs and Natural Products", Journal of Virology, 77(19): 10288-10294, 2003.

Lashuel et al. "New Class of Inhibitors of Amyloid-β Fibril Formation. Implications for the Mechanism of Pathogenesis in Alzheimer's Disease", The Journal of Biological Chemistry, 277(45): 42881-42890, 2002.

Oza et al. "Synthesis and Evaluation of Anthranilic Acid-Based Transthyretin Amyloid Fibril Inhibitors", Bioorganic & Medicinal Chemistry Letters, 9: 1-6, 1999.

Peterson et al. "Inhibiting Transthyretin Conformational Chamges That Lead to Amyloid Fibril Formation", Proc. Natl. Acad. Sci. USA, 95: 12956-12960, 1998.

Inglot "Comparison of the Antiviral Activity In Vitro of Some Non-Steroidal Anti-Inflammatory Drugs", Journal of General Virology, 4(2): 203-214, 1969.

Pavia et al. "Antimicrobial Activity of Nicotine Against a Spectrum of Bacterial and Fungal Pathogens", Journal of Medical Microbiology, 49(7): 675-676, 2000.

Westwater et al. "Use of Genetically Engineered Phage to Deliver Antimicrobial Agents to Bacteria: An Alternative Therapy for Treatment of Bacterial Infections", Antimicrobial Agents and Chemotherapy, 47 (4): 1301-1307, 2003.

Examiner's Report Dated Feb. 17, 2009 From the Australian Government, IP Australia Re.: Application No. 2004203461.

Office Action Dated Feb. 1, 2009 From the Israeli Patent Office Re.: Application No. 163285 and Its Translation Into English.

Office Action Dated Jan. 8, 2009 From the Israeli Patent Office Re.: Application No. 172788 and Its Translation Into English.

Office Action Dated Jan. 13, 2009 From the Government of India, Patent Office Re.: Application No. 1400/CHENP/2006.

Official Action Dated Feb. 24, 2009 From the US Patent and Trademark Office Re.: U.S. Appl. No. 11/660,522.

Official Action Dated Nov. 26, 2008 From the US Patent and Trademark Office Re.: U.S. Appl. No. 11/662,136.

Alic "Multiple Myeloma", Medical Network Inc., HealthAtoZ.com, 11 P., 2002. URL: http://www.lifesteps.com/gm/Atoz/ency/multiple_myeloma.jsp.

Chyan et al. "Potent Neuroprotective Properties Against the Alzheimer β-Amyloid by an Endogenous Melatonin-Related Indole Structure, Indole-3-Propionic Acid", The Journal of Biological Chemistry, 274(31): 21937-21942, Jul. 30, 1999.

Reza et al "Self-Assembling Organic Nanotubes Based on a Cyclic Peptide Architecture", Nature, 366: 324-327, 1993.

Sigma "Alphabetical List of Compounds: Phe-Phe, Phe-Pro, Phe-Val", Biochemicals and Reagents for Life Science Research, p. 774, 2000-2001.

Communication Pursuant to Article 94(3) EPC Dated Jun. 29, 2009 From the European Patent Office Re.: Application No. 05774727.1.

Examiner's Report Dated Jun. 22, 2009 From the Australian Government, IP Australia Re.: Application No. 2004203461.

Office Action Dated Jul. 14, 2009 From the Israeli Patent Office Re.: Application No. 169121 and Its Translation Into English.

Official Action Dated May 15, 2009 From the US Patent and Trademark Office Re.: U.S. Appl. No. 11/471,657.

Official Action Dated Jun. 22, 2009 From the US Patent and Trademark Office Re.: U.S. Appl. No. 12/318,653.

Search Results: STN File, Registry, RN 379722-40-4 and Following Dated Dec. 31, 2001 for the Australian Patent Application No. 2004203461.

Karle et al. "Structural Characteristics of α-Helical Peptide Molecules Contianing Aib Residues", Biochemistry, 29(29): 6747-6756, Jul. 24, 1990.

Soto et al. "Inhibition of Alzheimer's Amyloidosis by Peptides That Prevent β-Sheet Conformation", Biochemical and Biophysical Research Communications, 226(3): 672-680, 1996.

Toniolo et al. "Control of Peptide Conformation by the Thorpe-Ingold Effect (Cα-Tetrasubstitution)", Biopolymers (Peptide Science), 60(6): 396-419, 2001.

Communication Pursuant to Article 94(3) EPC Dated Sep. 25, 2009 From the European Patent Office Re.: Application No. 04770561.1.

Response Dated Jan. 21, 2010 to Communication Pursuant to Article 94(3) EPC of Sep. 25, 2009 From the European Patent Office Re.: Application No. 04770561.1.

Translation of Notice of Reason for Rejection Dated Sep. 10, 2010 From the Japanese Patent Office Re. Application No. 2006-527571.

Communication Pursuant to Article 94(3) EPC Dated Jun. 7, 2011 From the European Patent Office Re.: Application No. 04770561.1.

Communication Pursuant to Article 94(3) EPC Dated Aug. 22, 2008 From the European Patent Office Re.: Application No. 04770561.1.

Examination Report Dated Mar. 20, 2008 From the Government of India, Patent Office Re.: Application No. 1400/CHENP/2006.

International Search Report Dated Feb. 23, 2005 From the International Searching Authority Re.: Application No. PCT/IL2004/000890.

Asgharnejad "Ester Derivatives as Prodrugs", Transport Processes in Pharmaceutical Systems, 102: 186, 2000.

Patani et al. "Bioisosterism: A Rational Approach in Drug Design", Chemical Reviews, 96(8): 3147-3176, 1996.

Reddy et al. "Involvement of Maillard Reactions in Alzheimer Disease", Neurotoxicity Research, 4(3): 191-209, 2002.

Response Dated Jan. 3, 2011 to Notice of Reason for Rejection of Sep. 10, 2010 From the Japanese Patent Office Re. Application No. 2006-527571.

Response Dated May 17, 2011 to Notice of Reason for Rejection of Feb. 4, 2011 From the Japanese Patent Office Re. Application No. 2006-527571.
Translation of Notice of Reason for Rejection Dated Jun. 17, 2011 From the Japanese Patent Office Re. Application No. 2006-527571.
Translation of Notice of Reason for Rejection of Feb. 4, 2011 From the Japanese Patent Office Re. Application No. 2006-527571.
Translation of Notice of Reason for Rejection Dated Sep. 30, 2011 From the Japanese Patent Office Re. Application No. 2006-527571.
Communication Pursuant to Article 94(3) EPC Dated Mar. 12, 2008 From the European Patent Office Re.: Application No. 05774727.1.
Communication Pursuant to Article 96(2) Dated Jul. 17, 2006 From the European Patent Office Re.: Application No. 03777149.0.
Communication Pursuant to Rules 109 and 110 EPC Dated Aug. 18, 2005 From the European Patent Office Re.: Application No. 04700494.0.
Examination Report Jan. 13, 2009 From the Government of India, Patent Office Re.: Application No. 1400/CHENP/2006.
International Preliminary Report of Patentability Dated Mar. 17, 2006 From the International Preliminary Examining Authority Re.: Application No. PCT/IL2004/000890.
International Preliminary Report on Patentability Jan. 22, 2009 From the International Bureau of WIPO Re.: Application No. PCT/IL2005/000954.
International Preliminary Report on Patentability Dated Mar. 1, 2007 From the International Bureau of WIPO Re.: Application No. PCT/IL2005/000902.
International Preliminary Report on Patentability Dated Apr. 13, 2006 From the International Bureau of WIPO Re.: Application No. PCT/IL2004/000898.
International Preliminary Report on Patentability Dated Feb. 15, 2007 From the International Bureau of WIPO Re.: Application No. PCT/IL2005/000589.
International Preliminary Report on Patentability Dated Jan. 22, 2009 From the International Bureau of WIPO Re.: Application No. PCT/IL2004/000577.
International Preliminary Report on Patentability Dated Apr. 24, 2008 From the International Bureau of WIPO Re.: Application No. PCT/IL2006/001174.
International Preliminary Report on Patentability Dated Jan. 25, 2007 From the International Bureau of WIPO Re.: Application No. PCT/IL2005/000754.
OA Feb. 1, 2009 W Sec 9.
OA of Jan. 8, 2009 W Sec 8.
Official Action Dated Feb. 23, 2006 From the US Patent and Trademark Office Re.: U.S. Appl. No. 10/235,852.
Official Action Dated May 2, 2008 From the US Patent and Trademark Office Re.: U.S. Appl. No. 11/656,542.
Official Action Dated Apr. 3, 2009 From the US Patent and Trademark Office Re.: U.S. Appl. No. 11/662,136.
Official Action Dated Dec. 16, 2008 From the US Patent and Trademark Office Re.: U.S. Appl. No. 10/562,852.
Official Action Dated Apr. 19, 2006 From the US Patent and Trademark Office Re.: U.S. Appl. No. 10/901,243.
Official Action Dated Sep. 19, 2007 From the US Patent and Trademark Office Re.: U.S. Appl. No. 11/148,262.
Official Action Dated Sep. 27, 2007 From the US Patent and Trademark Office Re.: U.S. Appl. No. 11/148,266.
Partial European Search Report and the European Search Opinion Dared Apr. 16, 2009 From the European Patent Office Re.: Application No. 09002048.8.
Response Dated May 25, 2007 to Communication Pursuant to Article 94(3) of Jan. 18, 2007 From the European Patent Office Re.: Application No. 04700494.0.
Supplementary European Search Report Dated Apr. 18, 2006 From the European Patent Office Re.: Application No. 03704977.2.
Written Opinion Dated Jun. 15, 2006 From the International Preliminary Examining Authority Re.: Application No. PCT/IL03/00079.
International Search Report Dated May 10, 2004 From International Searching Authority Re.: Application No. PCT/IL2004/000012.
International Search Report Dated Aug. 16, 2005 From the International Searching Authority Re.: Application No. PCT/IL2004/000898.
International Search Report Dated Jul. 19, 2004 From the International Searching Authority Re.: Application No. PCT/IL03/01045.
Notice of Allowance Dated Sep. 16, 2008 From the US Patent Office Re.: U.S. Appl. No. 11/148,262.
Office Action Dated Sep. 15, 2008 From the Israeli Patent Office Re.: Application No. 169121 and Its Translation Into English.
Office Action Dated Sep. 15, 2008 From the Israeli Patent Office Re.: Appliction No. 169120 and Its Translation Into English.
Official Action Dated Dec. 3, 2008 From the US Patent and Trademark Office Re.: U.S. Appl. No. 10/574,405.
Official Action Dated Dec. 12, 2008 From the US Patent and Trademark Office Re.: U.S. Appl. No. 11/656,542.
Written Opinion Not Dated From the International Searching Authority Re.: Application No. PCT/IL2004/000898, Aug. 2005.
Reza et al "Self-assembling Organic Nanotubes Based on a Cyclic Peptide Architecture", Nature 366:324-327 (1993).
Sano "Prevention of Alzheimer's Disease: Where We Stand", Current Neurology and Neuroscience Reports, 2(5): 392-399, Oct. 2002. Abstract.

* cited by examiner

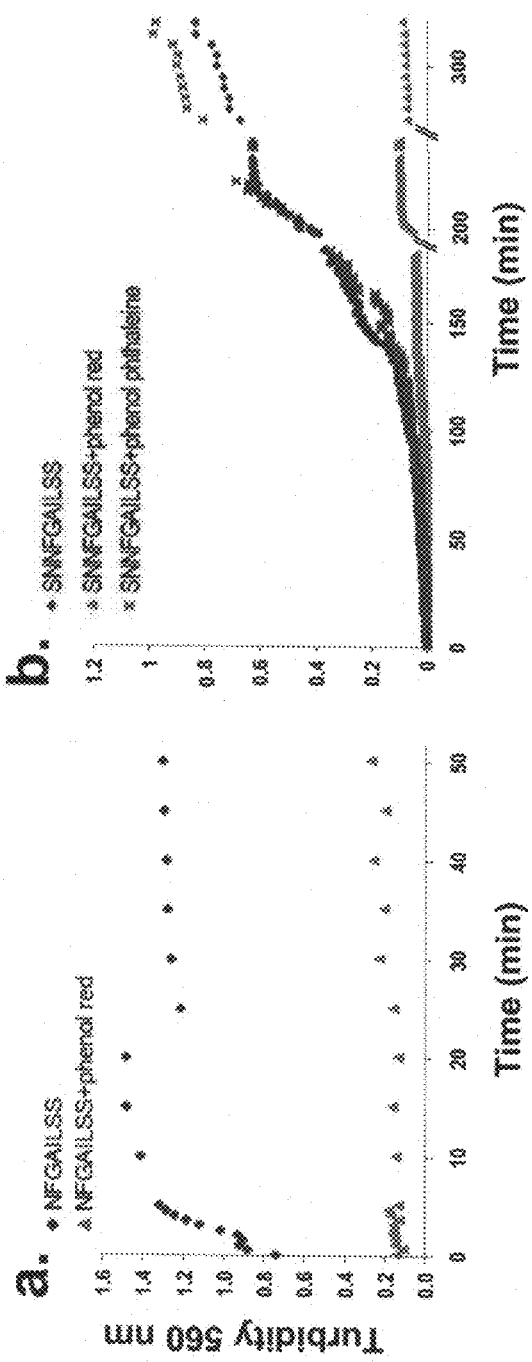
Figures 1a-b

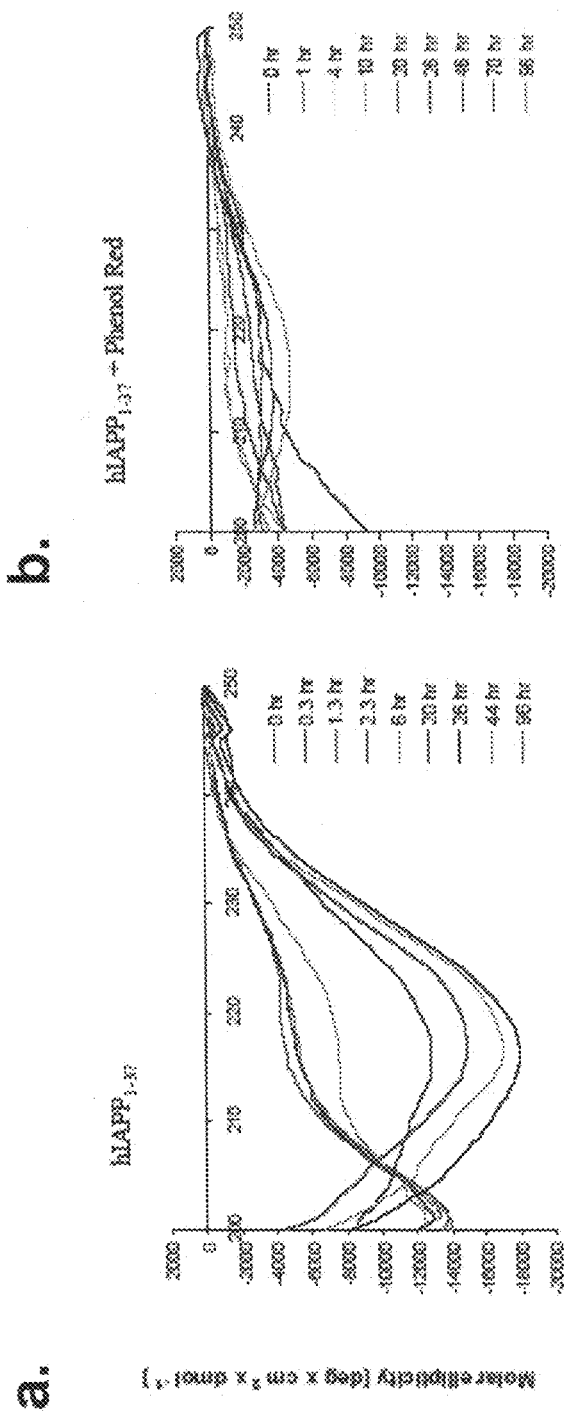
Figures 2a-b

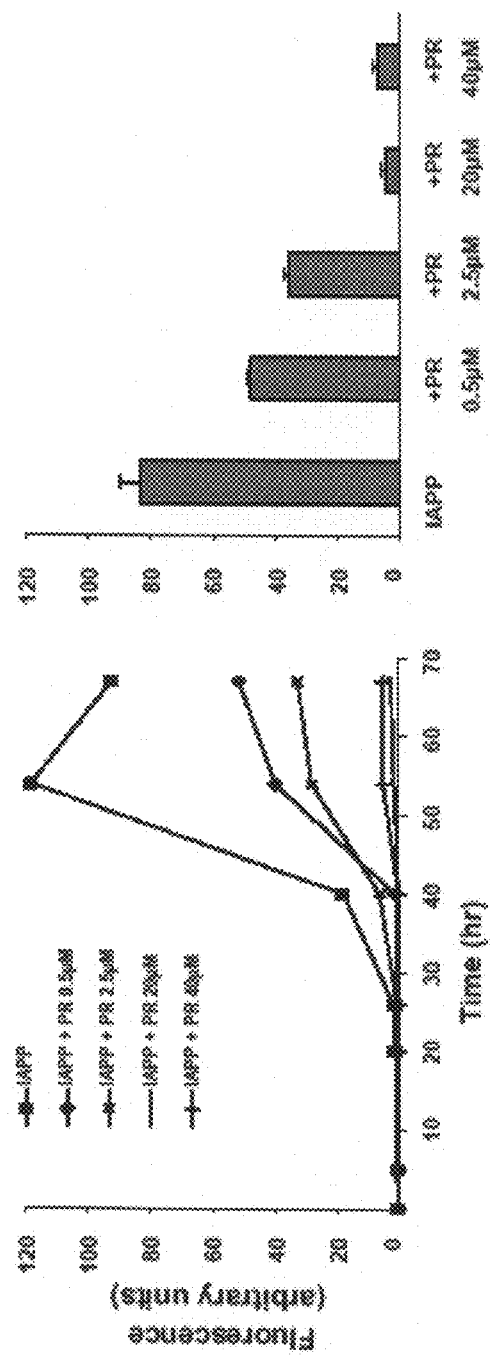

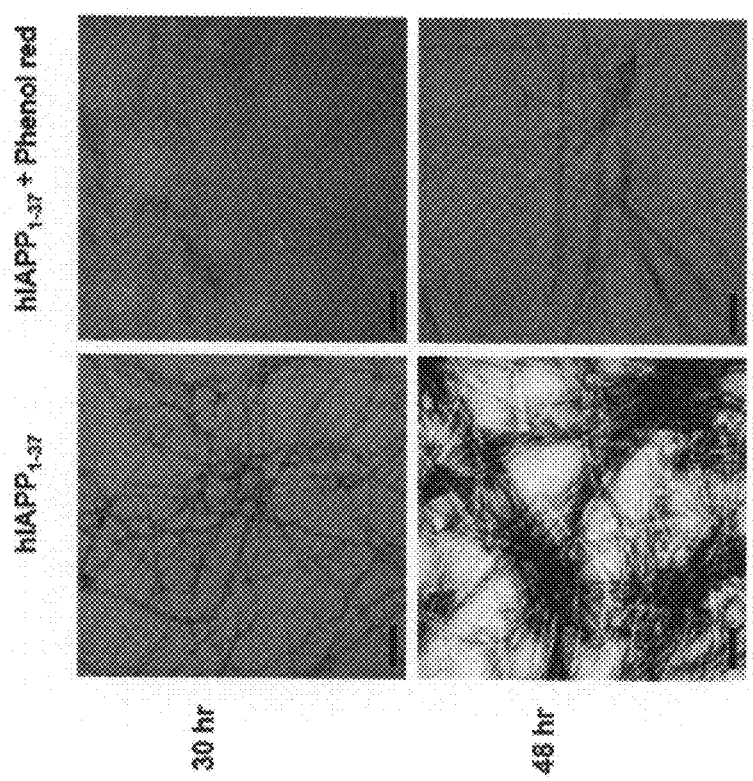

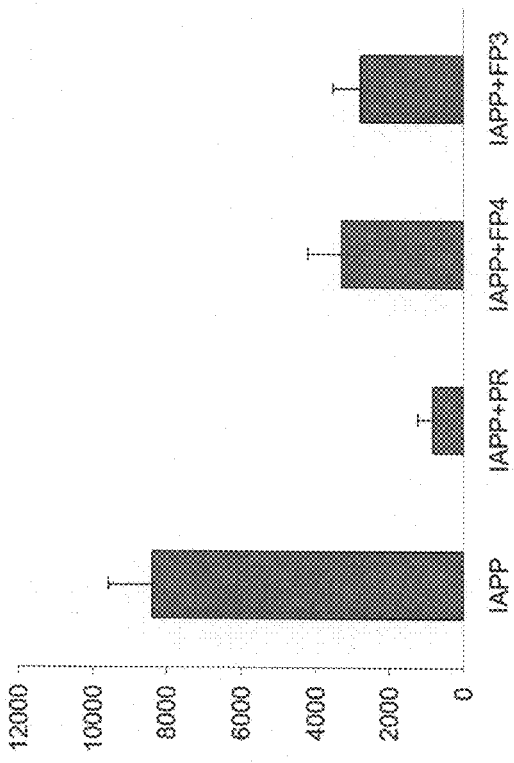
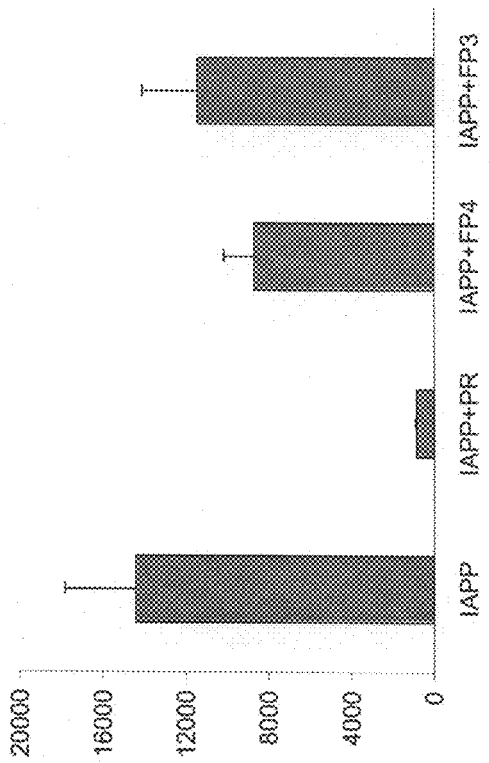
Figure 8a
Figure 8b

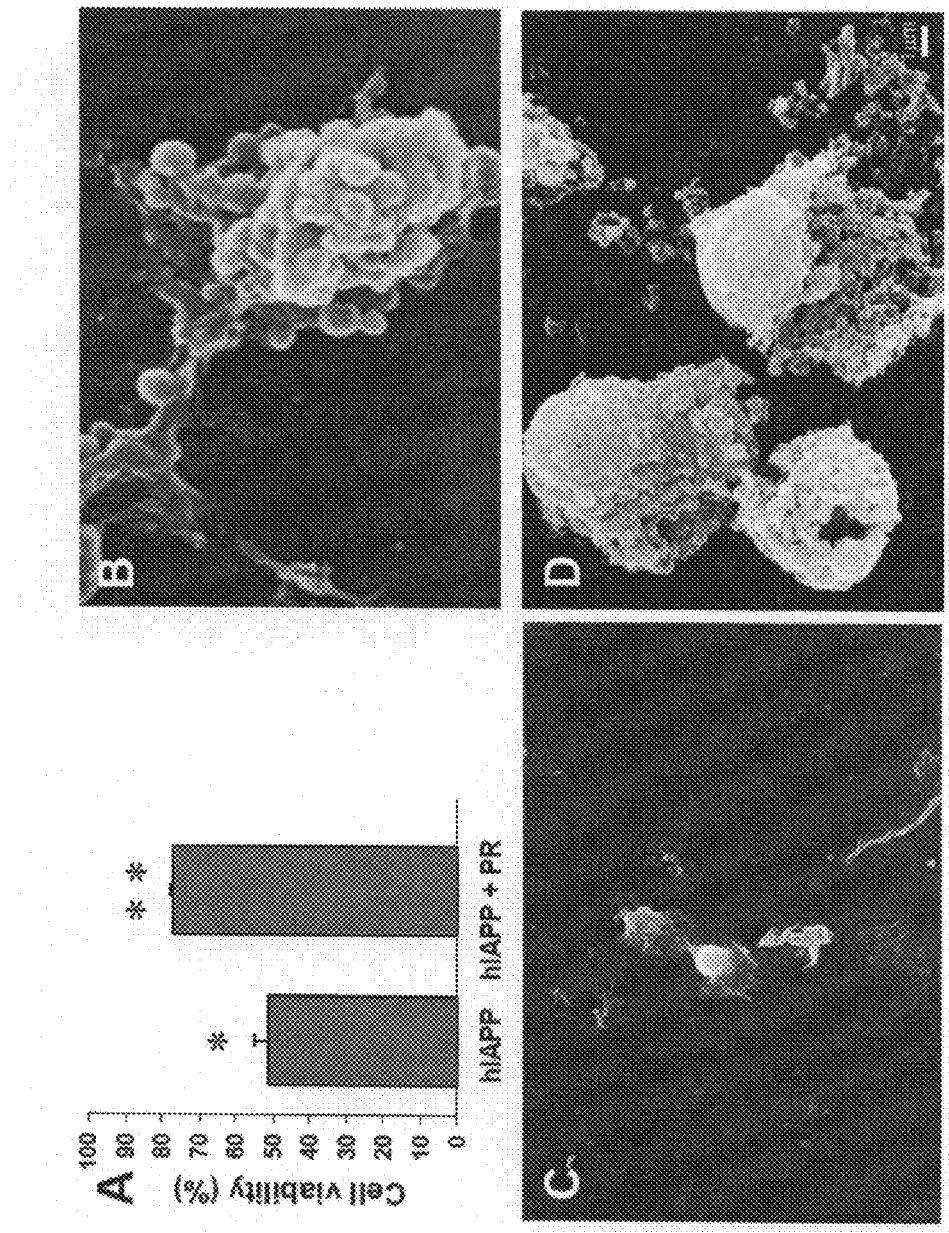
Figures 10a-d

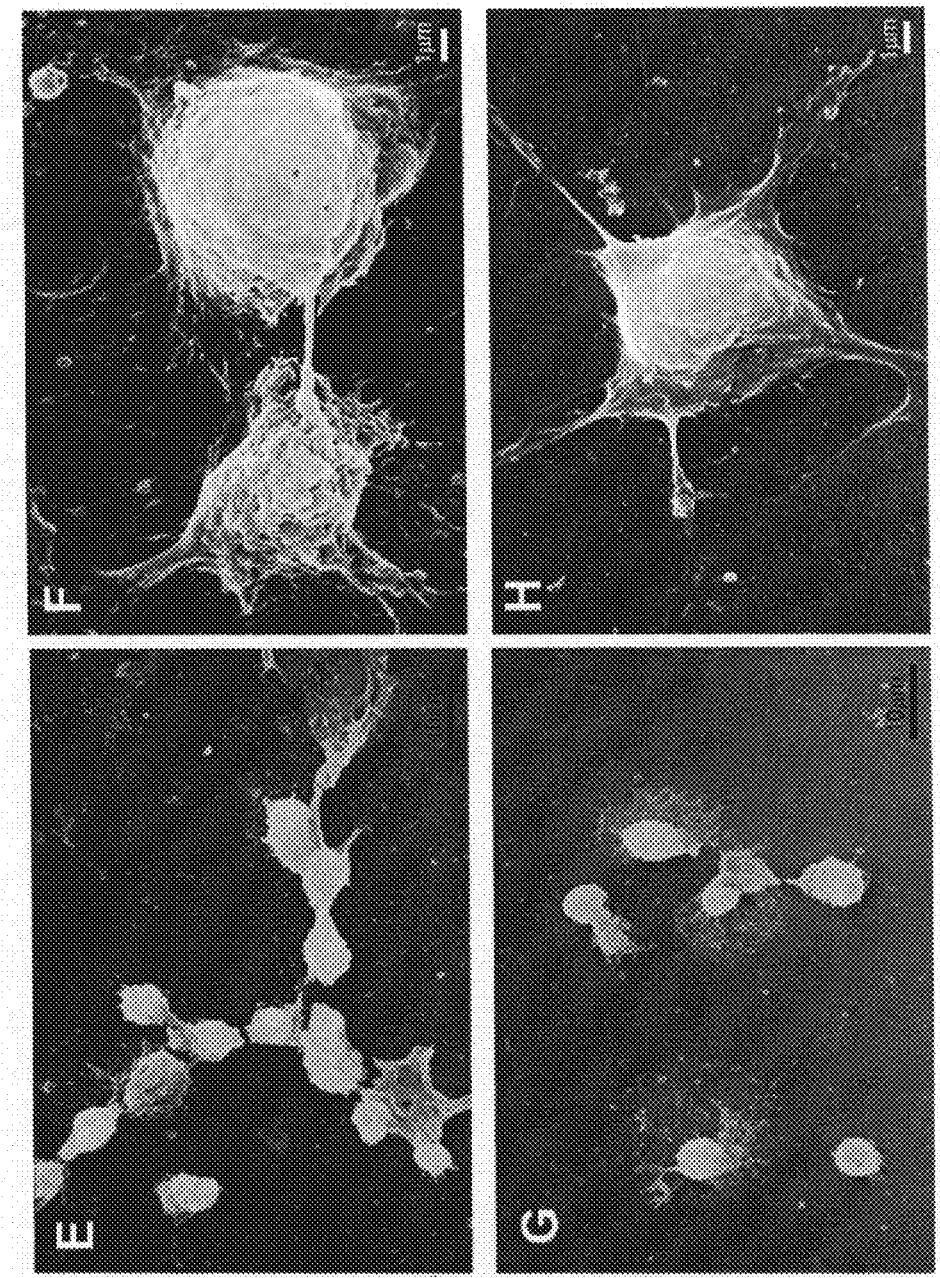
Figures 10e-h

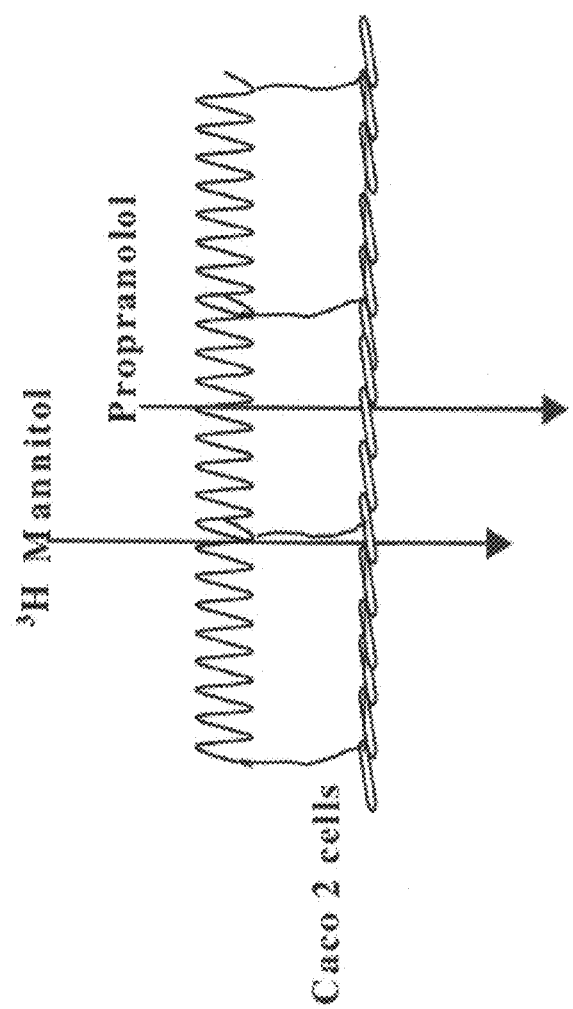

SEQUENCE LISTING

<160> NUMBER OF SEQ ID NOS: 3

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Asn Phe Gly Ala Ile Leu Ser Ser
1               5

<210> SEQ ID NO 2
<211> LENGTH: 10
<212> TYPE: PRT
<213> ORGANISM: Artificial sequence
<220> FEATURE:
<223> OTHER INFORMATION: Synthetic peptide

<400> SEQUENCE: 2

Ser Asn Asn Phe Gly Ala Ile Leu Ser Ser
1               5                   10

<210> SEQ ID NO 3
<211> LENGTH: 37
<212> TYPE: PRT
<213> ORGANISM: Artificial sequence
<220> FEATURE:
<223> OTHER INFORMATION: Synthetic peptide

<400> SEQUENCE: 3

Lys Cys Asn Thr Ala Thr Cys Ala Thr Gln Arg Leu Ala Asn Phe Leu
1               5                   10                  15

```
Val His Ser Ser Asn Asn Phe Gly Ala Ile Leu Ser Ser Thr Asn Val
            20                  25                  30

Gly Ser Asn Thr Tyr
            35
```

COMPOSITIONS AND METHODS USING SAME FOR TREATING AMYLOID-ASSOCIATED DISEASES

RELATED APPLICATIONS

This application is a continuation-in-part of PCT Patent Application No. PCT/IL2004/000890, filed on Sep. 23, 2004, which claims the benefit of U.S. Provisional Patent Application No. 60/505,425, filed on Sep. 25, 2003, U.S. Provisional Patent Application No. 60/553,953, filed on Mar. 18, 2004, and U.S. Provisional Patent Application No. 60/588,362, filed on Jul. 16, 2004. The contents of the above applications are all incorporated by reference.

FIELD AND BACKGROUND OF THE INVENTION

The present invention relates to compounds, compositions containing same and methods using same for preventing amyloid fibril formation. More particularly, the present invention relates to the use of polyaromatic compounds such as phenol red and novel derivatives thereof for the treatment of amyloid-associated diseases.

Amyloid material deposition (also referred to as amyloid plaque formation) is a central feature of a variety of unrelated pathological conditions including Alzheimer's disease, prion-related encephalopathies, type II diabetes mellitus, familial amyloidosis and light-chain amyloidosis.

Amyloid material is composed of a dense network of rigid, nonbranching proteinaceous fibrils of indefinite length that are about 80 to 100 Å in diameter. Amyloid fibrils contain a core structure of polypeptide chains arranged in antiparallel β-pleated sheets lying with their long axes perpendicular to the long axis of the fibril [Both et al. (1997) Nature 385:787-93; Glenner (1980) N. Eng. J. Med. 302:1283-92].

Approximately twenty amyloid fibril proteins have been identified in-vivo and correlated with specific diseases. These proteins share little or no amino acid sequence homology, however the core structure of the amyloid fibrils is essentially the same. This common core structure of amyloid fibrils and the presence of common substances in amyloid deposits suggest that data characterizing a particular form of amyloid material may also be relevant to other forms of amyloid material and thus can be implemented in template design for the development of drugs against amyloid-associated diseases such as type II diabetes mellitus, Alzheimer's dementia, or prion-related encephalopathies.

Furthermore, amyloid deposits do not appear to be inert in vivo, but rather are in a dynamic state of turnover and can even regress if the formation of fibrils is halted [Gillmore et al. (1997) Br. J. Haematol. 99:245-56].

Thus, therapies designed to inhibiting the production of amyloid polypeptides or inhibiting amyloidosis may be useful for treating amyloid associated diseases.

Inhibition of amyloid polypeptides production—Direct inhibition of the production of amyloid polypeptides may be accomplished, for example, through the use of antisense oligonucleotides such as against human islet amyloid polypeptide messenger RNA (mRNA). In vitro, the addition of antisense oligonucleotides or the expression of antisense complementary DNA against islet amyloid polypeptide mRNA increased the insulin mRNA and protein content of cells, demonstrating the potential effectiveness of this approach [Kulkarni et al. (1996) J. Endocrinol. 151:341-8; Novials et al. (1998) Pancreas 17:182-6]. However, no experimental results demonstrating the in vivo effectiveness of such antisense molecules have been demonstrated.

Inhibition of amyloid fibril formation—Amyloid, including islet amyloid, contains potential stabilizing or protective substances, such as serum amyloid P component, apolipoprotein E, and perlecan. Blocking their binding to developing amyloid fibrils could inhibit amyloidogenesis [Kahn et al. (1999) Diabetes 48:241-53], as could treatment with antibodies specific for certain parts of an amyloidogenic protein [Solomon et al. (1997) Proc. Natl. Acad. Sci. USA 94:4109-12].

The following summarizes current attempts to engineer drugs having the capability of destabilizing amyloid structures.

Destabilizing compounds—Heparin sulfate has been identified as a component of all amyloids and has also been implicated in the earliest stages of inflammation-associated amyloid induction. Kisilevsky and co-workers (Nature Med. 1:143-148, 1995) described the use of low molecular weight anionic sulfonate or sulfate compounds that interfere with the interaction of heparin sulfate with the inflammation-associated amyloid precursor and the peptide of Alzheimer's disease (AD). Heparin sulfate specifically influences the soluble amyloid precursor (SAA2) to adopt an increased β-sheet structure characteristic of the protein-folding pattern of amyloids. These anionic sulfonate or sulfate compounds were shown to inhibit heparin accelerated Aβ fibril formation and were able to disassemble preformed fibrils in vitro, as monitored by electron micrography. Moreover, these compounds substantially arrested murine splenic inflammation-associated amyloid progression in vivo in acute and chronic models. However, the most potent compound [i.e., poly-(vinylsulfonate)] showed acute toxicity. Similar toxicity has been observed with another compound, IDOX (Anthracycline 4'-iodo-4'-deoxy-doxorubicin), which has been observed to induce amyloid resorption in patients with immunoglobin light chain amyloidosis (AL) [Merlini et al. (1995) Proc. Natl. Acad. Sci. USA].

Destabilizing antibodies—Anti-β-amyloid monoclonal antibodies have been shown to be effective in disaggregating β-amyloid plaques and preventing β-amyloid plaque formation in vitro (U.S. Pat. No. 5,688,561). However, no experimental results demonstrating the in vivo effectiveness of such antibodies have been demonstrated.

Small molecules—The potential use of small molecules which bind the amyloid polypeptide and stabilizing the native fold of the protein has been attempted in the case of the transthyretin (TTR) protein [Peterson (1998) Proc. Natl. Acad. Sci. USA-95:12965-12960; Oza (1999) Bioorg. Med. Chem. Lett. 9:1-6]. Thus far, it has been demonstrated that molecules such as thyroxine and flufenamic acid are capable of preventing the conformation change, leading to amyloid formation. However, the use of the compounds in animal models has not been proved yet and might be compromised due to the presence in blood or proteins, other than TTR, capable of binding these ligands.

Antioxidants—Another proposed therapy has been the intake of antioxidants in order to avoid oxidative stress and maintain amyloid proteins in their reduced state (i.e., monomers and dimers). The use of sulfite was shown to lead to more stable monomers of the TTR both in vitro and in vivo [Altland (1999) Neurogenetics 2:183-188]. However, a complete characterization of the antioxidant effect is still not available and the interpretation of results concerning possible therapeutic strategies remains difficult.

Destabilizing peptides—The finding that the addition of synthetic peptides that disrupt the β-pleated sheets ("β-sheet breakers") dissociated fibrils and prevented amyloidosis [Soto et al. (1998) Nat. Med. 4:822-826] is particularly promising from a clinical point of view. In brief, a penta-residue peptide inhibited amyloid beta-protein fibrillogenesis, disassembled preformed fibrils in vitro and prevents neuronal death induced by fibrils in cell culture. In addition, the beta-sheet breaker peptide significantly reduced amyloid beta-protein deposition in vivo and completely blocked the formation of amyloid fibrils in a rat brain model of amyloidosis.

Green tea extracts—U.S. Patent Applications having the Publication Nos. 20020086067 and 20020151506 teach the use of various components of green tea extracts for treating an amyloid disease. While these patent applications teach that these components inhibit amyloid fibril formation, they fail to teach neither a mechanism nor a common structural feature which provides these green tea components with such an activity.

The present inventors have previously shown that aromatic interactions play a key role in amyloid fibril formation by serving as structural and functional elements that direct molecular recognition and self-assembly.

While conceiving the present invention, it was therefore envisioned that compounds having a plurality (e.g., two or more) of aromatic moieties, which may participate in such aromatic interactions, could efficiently serve as inhibitors of amyloid fibril formation.

While reducing the present invention to practice, the present inventors indeed uncovered that amyloid formation can be strongly inhibited by polyaromatic compounds, such as phenol red (PR), suggesting use of these compounds in the treatment of amyloid-associated diseases.

SUMMARY OF THE INVENTION

According to one aspect of the present invention there is provided use of a compound having the general Formula I:

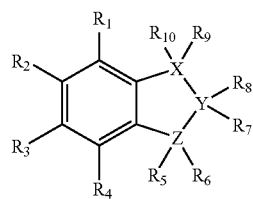

Formula I a pharmaceutically acceptable salt thereof or a prodrug thereof,
wherein:
X, Y and Z are each independently selected from the group consisting of carbon, oxygen, sulfur, $CR_{11}R_{12}$ or $R_{13}R_{14}C—CR_{15}R_{16}$, provided that at least one of X, Y and Z is oxygen or sulfur;
$R_1$—$R_{16}$ are each independently selected from the group consisting of hydrogen, lone pair electrons, hydroxy, alkyl, cycloalkyl, phenyl, alkoxyphenyl, thioalkoxyphenyl, aryloxyphenyl, thioaryloxyphenyl, carboxyphenyl, thiocarboxyphenyl, phenol, hydroxyphenol, dihydroxyphenol, aryl, alkenyl, alkynyl, heteroaryl, heteroalicyclic, halo, alkoxy, aryloxy, thiohydroxy, thioalkoxy, thioaryloxy, C-carboxy, O-carboxy, thiocarboxy, carbonyl, oxo, thiocarbonyl, sulfinyl, and sulfonyl, or absent, or, alternatively, at least two of $R_1$—$R_4$ and/or at least two of $R_5$—$R_{16}$ form at least one five- or six-membered aromatic, heteroaromatic, alicyclic or heteroalicyclic ring, whereas:
at least one of $R_1$—$R_4$ is selected from the group consisting of hydroxy, alkoxy, aryloxy, thiohydroxy, thioalkoxy, thioaryloxy, O-carboxy and O-thiocarboxy and/or at least one of $R_5$—$R_{16}$ comprises phenol, alkoxyphenyl, thioalkoxyphenyl, aryloxyphenyl, thioaryloxyphenyl, carboxyphenyl, thiocarboxyphenyl hydroxyphenol, and dihydroxyphenol,
for the manufacture of a medicament identified for the treatment of amyloid-associated diseases.

According to still further features in the described preferred embodiments, X is carbon; Y is oxygen; Z is carbon or sulfur; and at least one of $R_5$ and $R_6$ is oxo.

According to still further features in the described preferred embodiments at least one of $R_9$ and $R_{10}$ is selected from the group consisting of alkoxyphenyl, thioalkoxyphenyl, aryloxyphenyl, thioaryloxyphenyl, carboxyphenyl, thiocarboxyphenyl, phenol, hydroxyphenol and dihydroxyphenol.

According to still further features in the described preferred embodiments the compound is selected from the group consisting of phenol red, dimethoxy phenol red, methoxy phenol red, diacetoxy phenol red, acetoxy phenol red, pyrocatechol violet, phenolphthalein, hydroxyphenyl, and bromophenol red. In a preferred embodiment, the compound is diacetoxy phenol red.

According to another aspect of the present invention there is provided an article-of-manufacture comprising a packaging material and a pharmaceutical composition identified for treating amyloid-associated diseases being contained within the packaging material, the pharmaceutical composition including, as an active ingredient, the compound described hereinabove, and a pharmaceutically acceptable carrier.

According to yet another aspect of the present invention there is provided a method of treating an amyloid-associated disease in a subject, the method comprising administering to a subject in need thereof, a therapeutically effective amount of the compounds described hereinabove, thereby treating the amyloid-associated disease in the subject.

According to further features in preferred embodiments of the invention described below, the administering is effected at a concentration of the compound not exceeding 4 mg/Kg body weight/hour.

According to still further features in the described preferred embodiments the administering is effected orally.

According to still another aspect of the present invention there is provided a pharmaceutical composition comprising a therapeutically effective amount of the compound described hereinabove and a pharmaceutically acceptable carrier.

According to still further features in the described preferred embodiments the pharmaceutical composition further comprises an anti-amyloid drug.

According to still further features in the described preferred embodiments the anti-amyloid drug is selected from the group consisting of an amyloid-destabilizing antibody, an amyloid-destabilizing peptide and an anti-amyloid small molecule.

According to still further features in the described preferred embodiments the compound is diacetoxy phenol red and the pharmaceutical acceptable carrier comprises a mixture of polyethylene glycol, saturated sodium chloride and N,N-dimethylacetamide.

According to still further features in the described preferred embodiments the pharmaceutical composition is formulated for oral administration.

According to still further features in the described preferred embodiments the pharmaceutical composition is formulated for intravenous administration. According to still another aspect of the present invention there is provided a novel compound having the general Formula II:

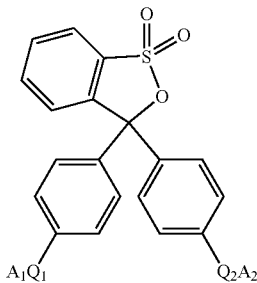

Formula II a pharmaceutically acceptable salt thereof or a prodrug thereof, wherein $Q_1$ and $Q_2$ are each independently selected from the group consisting of oxygen and sulfur; and $A_1$ and $A_2$ are each independently selected from the group consisting of hydrogen, alkyl, aryl, cycloalkyl and carbonyl, whereas when $Q_1$ and $Q_2$ are each oxygen, one of $A_1$ and $A_2$ is hydrogen and the other is selected from the group consisting of alkyl, cycloalkyl, aryl and carbonyl, preferably methyl or acetyl.

The present invention successfully addresses the shortcomings of the presently known configurations by providing compositions and methods using same for preventing amyloid fibril formation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 3A:
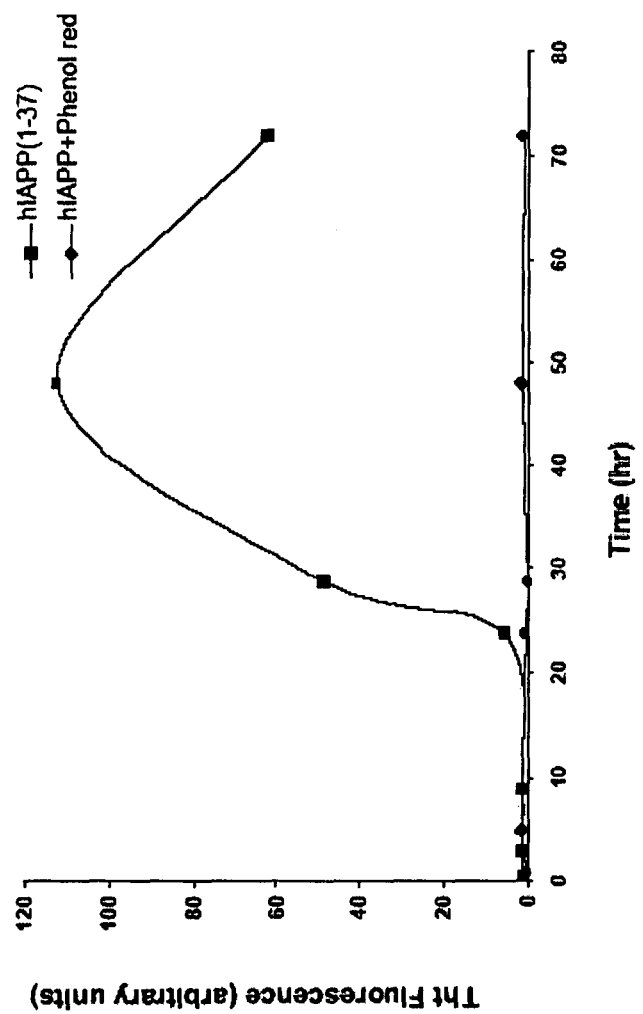
Figure 4A:
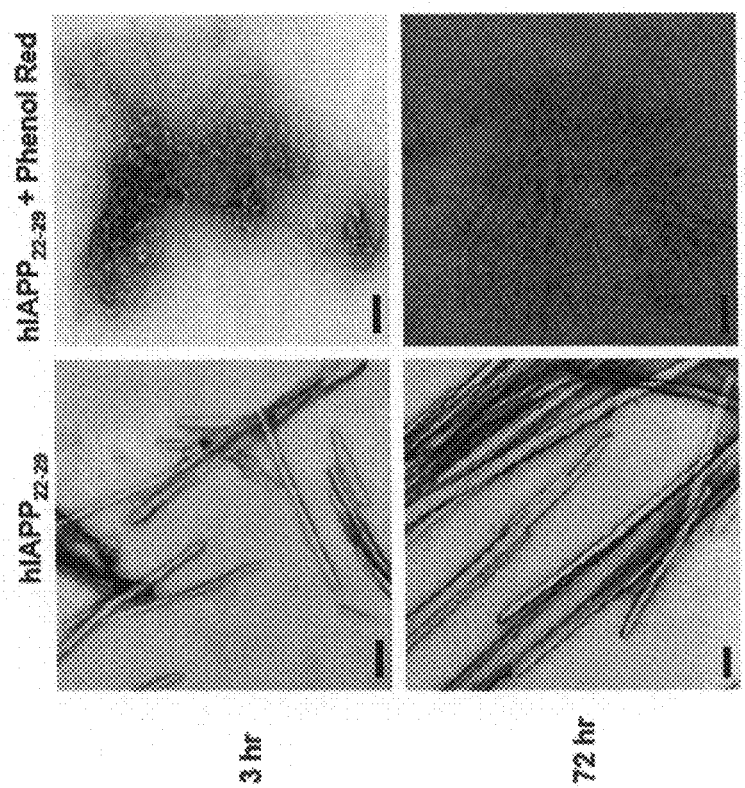
Figure 4B:
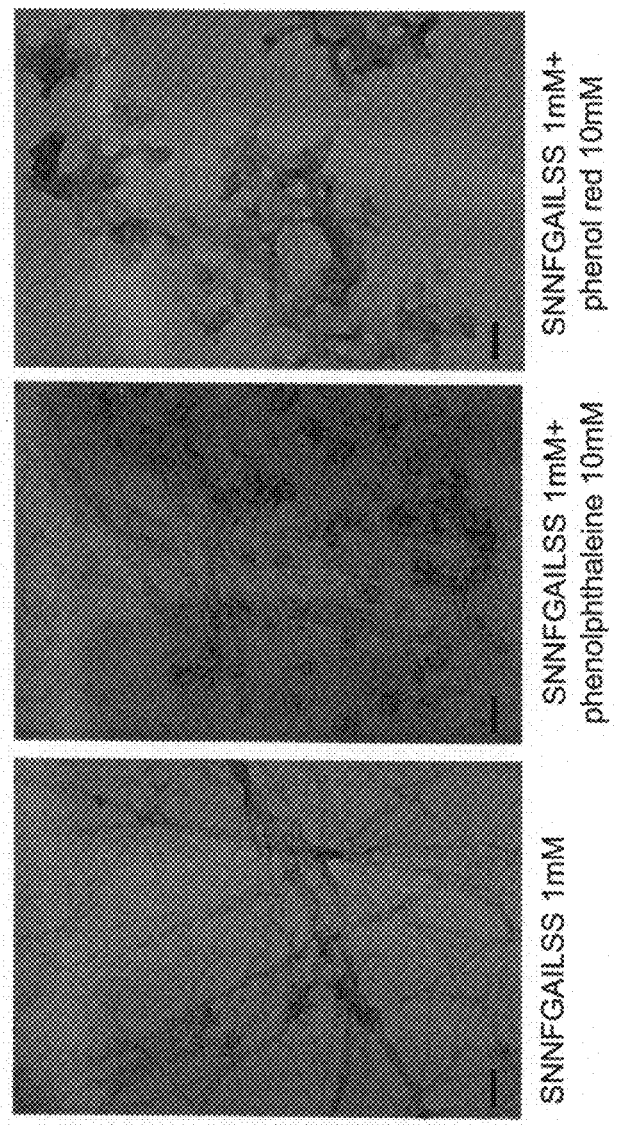
Figure 5A:
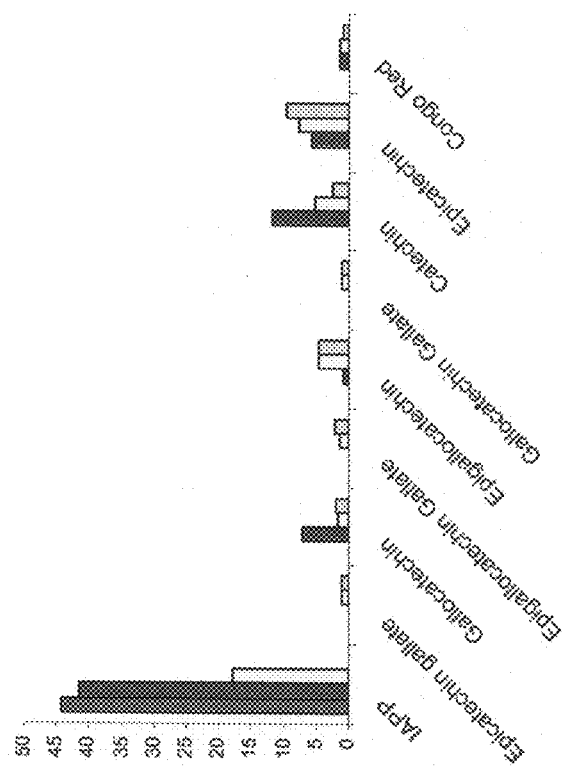
Figure 5B:
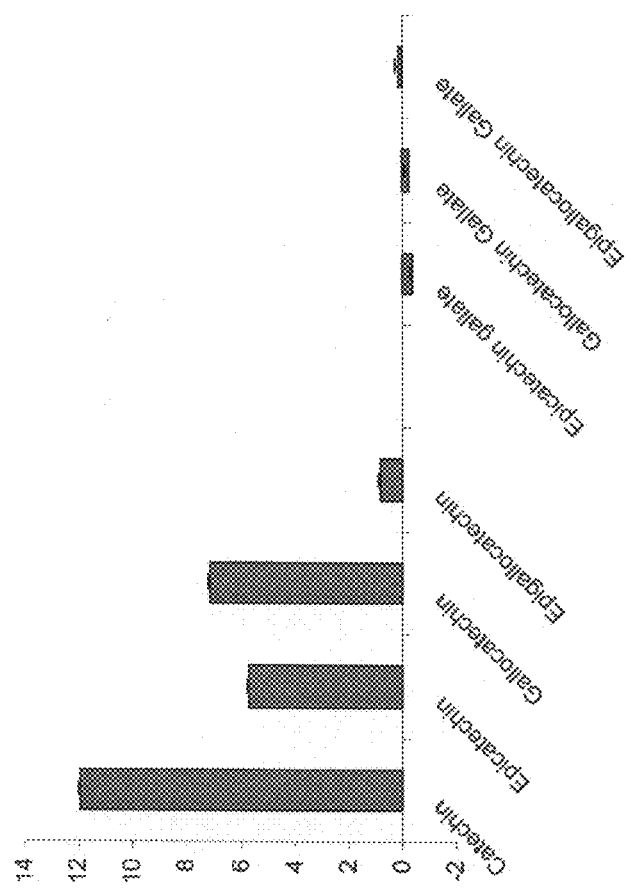
Figure 6:
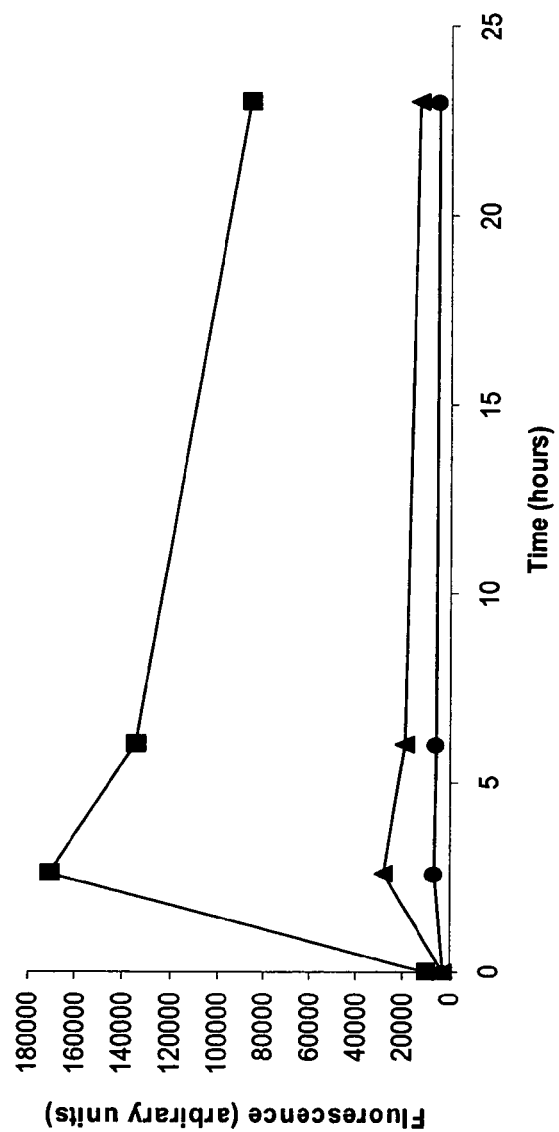
Figure 7:
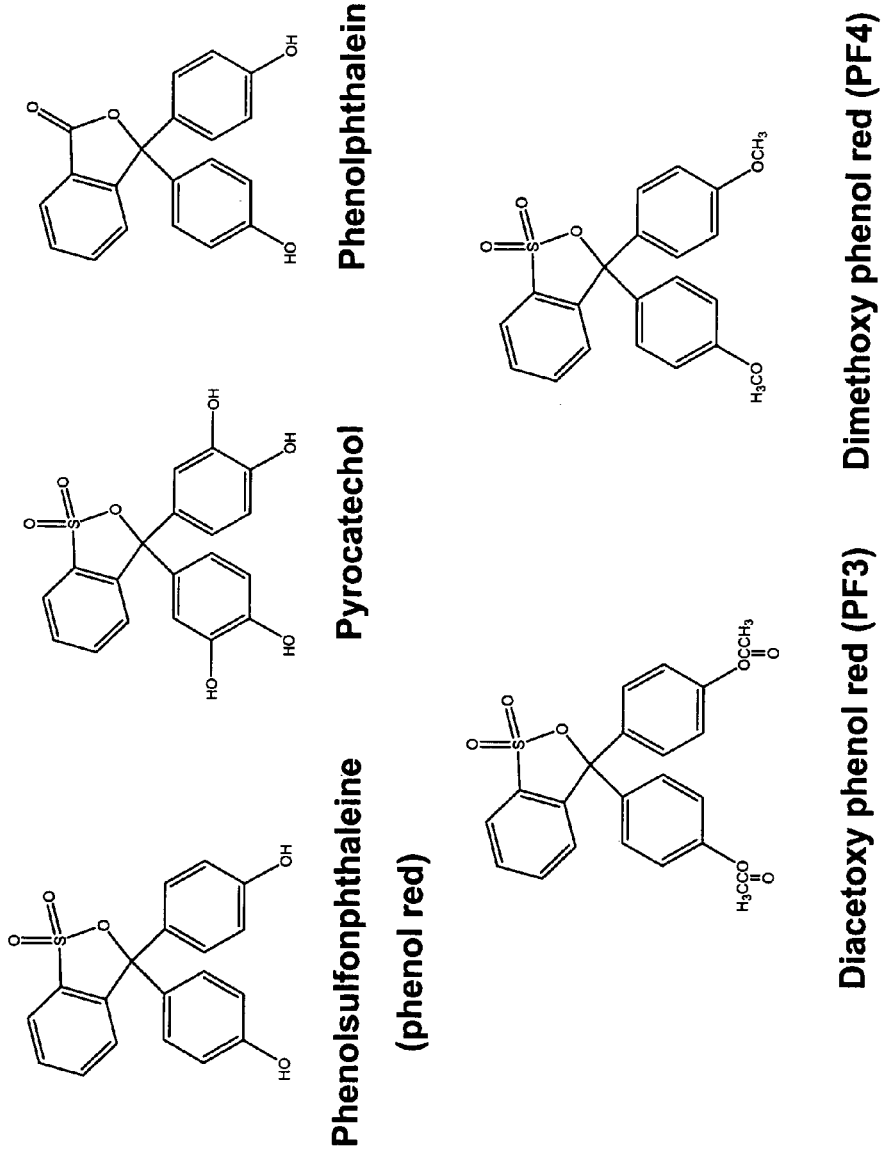
Figure 9:
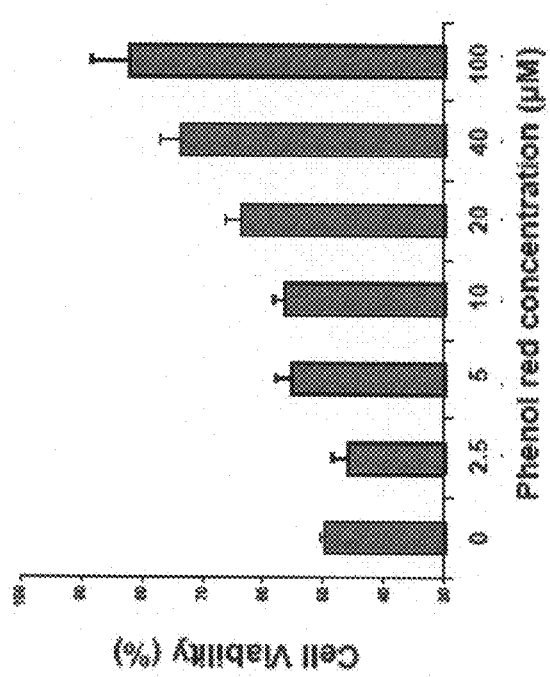
Figure 12:
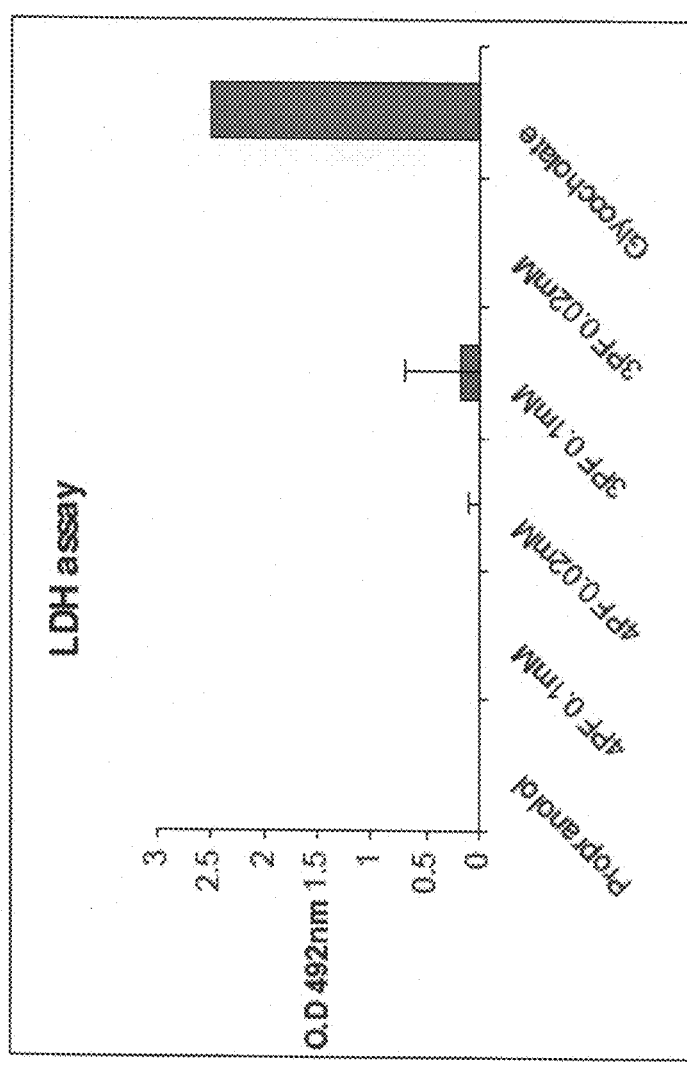
Figure 13:
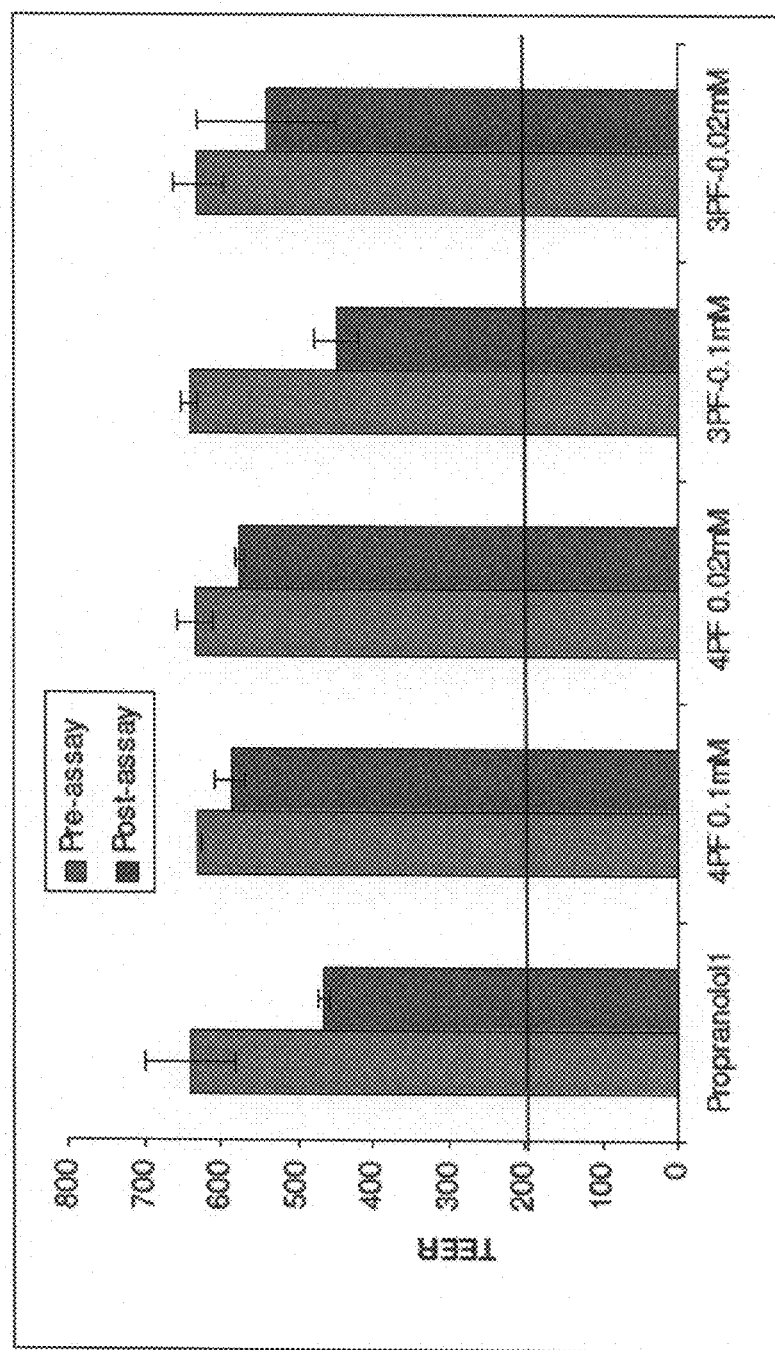
Figure 14:
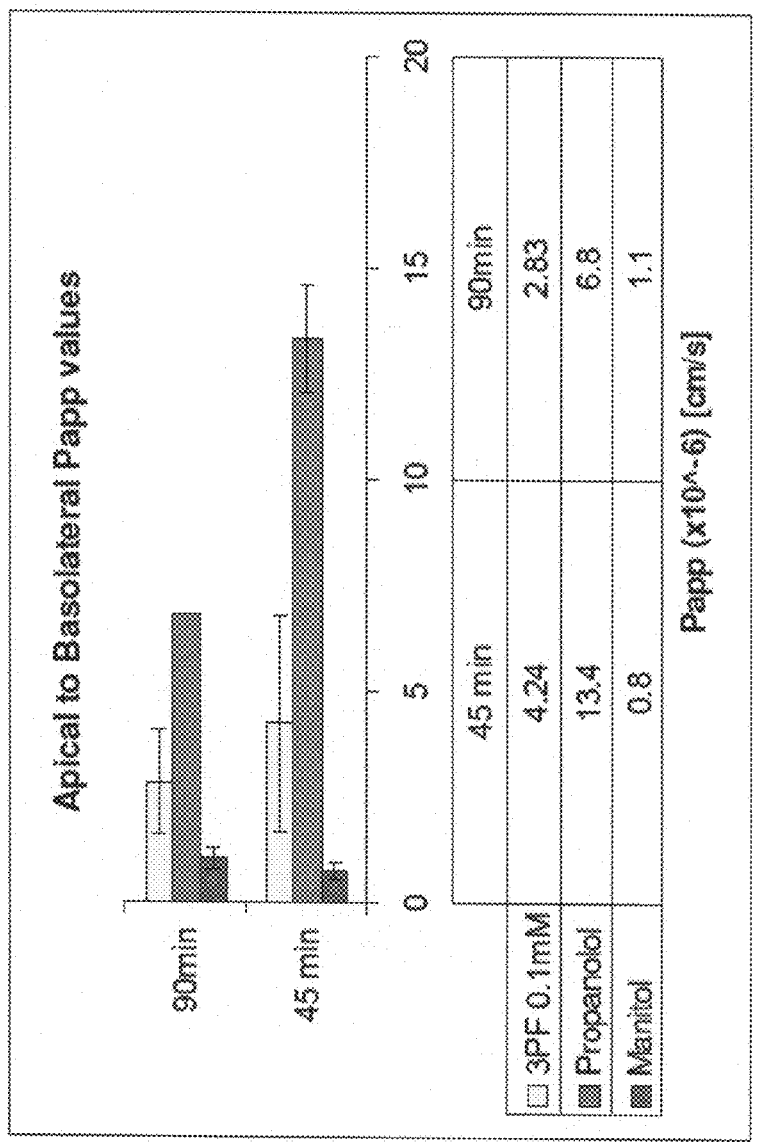
Figure 15:
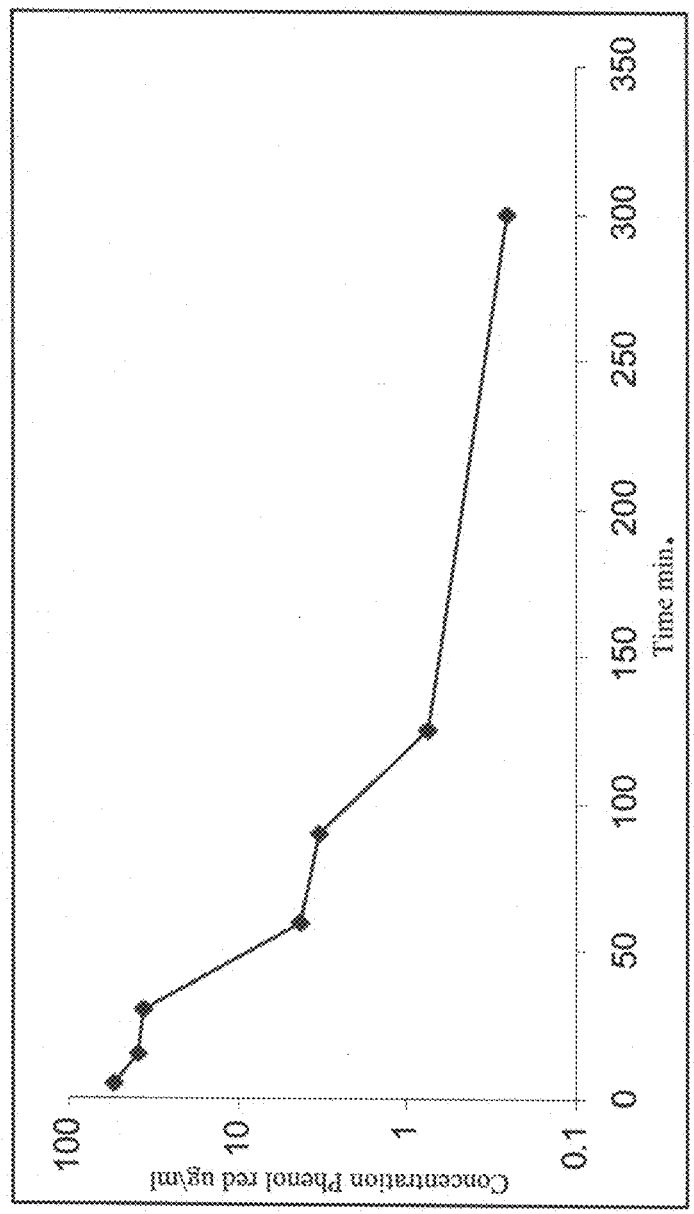
Figure 16:
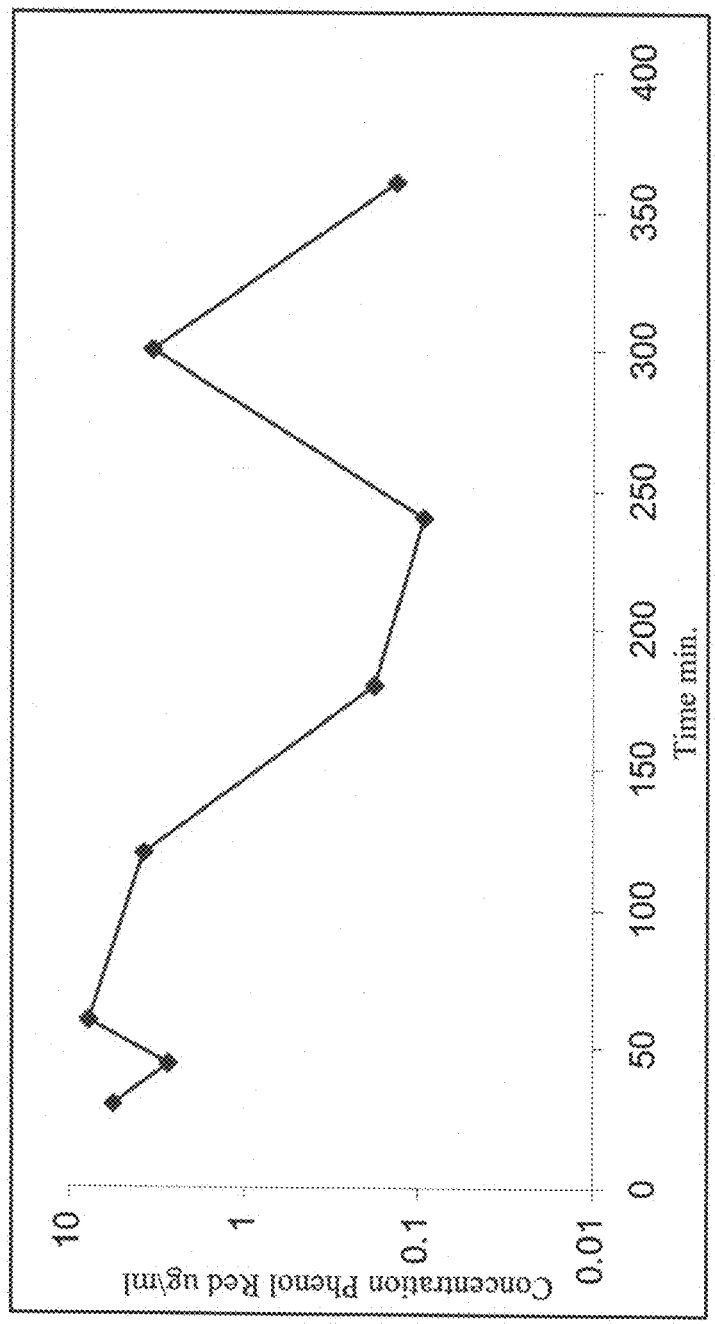

FIGS. 1a-b are graphs depicting inhibition of hIAPP core amyloidogenic peptide (hIAPP$_{22-29}$ and hIAPP$_{20-29}$) aggregation in the presence of phenol red. 1 mM peptide was dissolved in Tris buffer (pH 7.2) and 4% DMSO. Phenol red inhibitor was dissolved in the same buffer conditions to a final concentration of 10 mM. For each sample turbidity was measured continuously at 560 nm. FIG. 1a—hIAPP$_{22-29}$ (NF-GAILSS) aggregation. FIG. 1b—hIAPP$_{20-29}$ (SNNF-GAILSS) aggregation with phenolphthaleine as control. Background values of the buffer and phenol red were reduced from the relevant measurements;

FIGS. 2a-b are graphs depicting secondary structure transition of hIAPP$_{1-37}$ peptide in the absence (FIG. 2a) or presence (FIG. 2b) of phenol red, as measured using Circular Dichroism. Human hIAPP$_{1-37}$ was dissolved in HFIP and diluted into sodium acetate buffer (pH 6.5) to a final concentration of 4 µM and 1% HFIP with or without 40 µM phenol red. Non-soluble peptide was removed using centrifugation. Note that in the absence of inhibitor (FIG. 2a), hIAPP$_{1-37}$ shows a transition from random coil conformation within 6 hours, and this transition reaches a maximal value within 26 hours. However, in the presence of 40 µM phenol red inhibitor (FIG. 2b) there is an evident inhibition of transition to β sheet conformation (218 nm peak);

FIGS. 3a-c is a graph depicting the effect of phenol red on human IAPP$_{1-37}$ fibril formation, as determined by Thioflavin T fluorescence assay. FIG. 3a—Human IAPP$_{1-37}$ was dissolved in HFIP and diluted into sodium acetate buffer (pH 6.5) to a final concentration of 4 µM and 1% HFIP with or without 40 µM phenol red. Non-soluble peptide was separated using centrifugation. Fluorescence values were measured after the addition of 3 µM Tht to each sample. Note, following a lag phase of approximately 20 hours the fluorescence values increased significantly without inhibitor in contrast to constant low levels in the presence of the phenol red inhibitor. FIG. 3b—As in FIG. 3a only gradual concentration of phenol red was used along with a more sensitive fluorometer which enabled the dilution of the sample 10 folds so that maximal phenol red in the measured sample did not exceed 4 µM. As shown a dose dependent inhibition was evident with ~IC50 of 2.5 µM. FIG. 3c—Shows end point fluorescence of the samples of FIG. 3b following 5 days of incubation;

FIGS. 4a-c are photomicrographs depicting the morphology of hIAPP$_{22-29}$, hIAPP$_{20-29}$ peptides, and hIAPP$_{1-37}$ polypeptide in the absence or presence of phenol red and phenolphthaleine inhibitors. hIAPP$_{22-29}$ and hIAPP$_{20-29}$ peptides were prepared as described in FIGS. 1a-c and hIAPP$_{1-37}$ as in FIGS. 3a-c. Samples were generated by staining 10 µl sample with Uranyl acetate and then viewed with a JEOL 1200EX electron microscope operating at 80 kV. Distinct morphological differences are evident for all peptides, which showed a kinetic inhibitory effect of fibril formation by phenol red. In contrary, no inhibition effect was evident by phenolephthaleine molecule (FIG. 4b);

FIGS. 5a-b are histograms depicting inhibition of hIAPP fibril formation by green tea polyphenols, as determined by Tht fluorescence assay. Color code for FIG. 5a: Blue—48 hr., red 3 days, yellow—8 days, green 12—days. Note, detailed observation of the inhibitory effect following 3 days of incubation in the presence of green tea polyphenols (FIG. 5b) revealed high efficacy for the gallate group;

FIG. 6 presents comparative plots demonstrating the inhibition of hIAPP$_{1-37}$ fibril formation by pyrocatechol violet, as determined by ThT fluorescence assay (squares denote no addition of inhibitor, triangles denote addition of 4 µM pyrocatechol violet and circles denote addition of 40 µM pyrocatechol violet);

FIG. 7 presents the chemical structures (2D) of the inhibitors phenol red, pyrocatechol violet, phenolphthaleine, Diacetoxy phenol red (PF3) and Dimethoxyphenol red (PF4);

FIGS. 8a-b are histograms depicting inhibition of hIAPP$_{1-37}$ fibril formation by PF3 and PF4 as, determined by Thioflavin T fluorescence assay. Samples were either centrifuged immediately after dilution of hIAPP stock solution (FIG. 8a) or left uncentrifuged (FIG. 8b);

FIG. 9 is a bar graph showing a dose dependent rescue effect of phenol red on PC12 cells incubated in the presence of hIAPP$_{1-37}$. Values are mean±SD (n=4);

FIGS. 10a-h show the rescue effect of PR on pancreatic β-cells incubated in the presence of hIAPP aggregates. βTC-tet rodent β-cells were incubated for 24 hrs with 4 μM hIAPP$_{1-37}$ in serum free DMEM with or without phenol red. MTT reduction was measured after overnight incubation. FIG. 10a shows cell viability compared to cells incubated in the absence of hIAPP, in medium with or without phenol red, respectively. Values are mean±SD (n=4),* p=0.03, ** p<0.005. FIG. 10b-h are micrographs showing SEM analysis of β cells grown on microscope coverslips under the same conditions. FIGS. 10b-d show cells following the addition of hIAPP alone. These cells display membrane blebbing and collapse. FIGS. 10e-f show cells treated with hIAPP in the presence of 40 μM phenol red in the growth medium. FIGS. 10g-h show control cells not treated with hIAPP;

FIG. 11 presents a schematic illustration of a CaCo-2 monolayer system, showing the standards propranolol and mannitol pass via transcellular and paracellular routes, respectively (marked by arrows);

FIG. 12 is a bar graph presenting the lactate dehydrogenase (LDH) activity in basolateral buffer from the tested inserts, compared with the positive control glycocholate, measured in a colorimetric assay. Results are expressed as Mean±SD optical density (OD) values at 492 nm;

FIG. 13 is a bar graph presenting the CaCo-2 monolayer recoveries in the experimental transport inserts. TEER values were measured before (pre-assay) and 24 hours after transport experiment (post-assay) in all the inserts. Results are expressed as Mean TEER values (ohms/cm)±SD. The horizontal line represents recovery threshold;

FIG. 14 is a bar graph presenting the apparent permeability coefficients (Papp) of PF3 at apical to basolateral direction, as compared to Papp standards values (of mannitol and propranolol). 0.2 mM and 1 mM 3PF, $^3$H-mannitol and propranolol (n=2) standards were assayed in parallel. Samples from receiver chamber were removed at 45 and 90 minutes and analyzed in HPLC or counted with beta-scintillation counter. The data represent Papp mean values±standard deviation;

FIG. 15 presents the phenol red plasma profile following intravenous administration; and FIG. 16 presents the phenol red plasma profile following oral administration.

DESCRIPTION OF THE PREFERRED EMBODIMENTS

The present invention is of aromatic compounds which can be used in the treatment of amyloid-associated diseases, such as, for example, diabetes.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Numerous therapeutic approaches for prevention of amyloid fibril formation or disaggreagtion of amyloid material have been described in the prior art. However, current therapeutic approaches are limited by cytotoxicity, non-specificity and delivery barriers.

The present inventors have previously shown that aromatic interactions play a key role in amyloid fibril formation by serving as structural and functional elements that direct molecular recognition and self-assembly [Azriel and Gazit (2001) *J. Biol. Chem* 276: 34156-34161; Gazit (2002) *FASEB J.* 16:77-83]. Consequently, aromatic peptides were shown to inhibit amyloid-fibril formation.

While reducing the present invention to practice, the present inventors uncovered that amyloid formation can be strongly inhibited by aromatic compounds, such as phenol red (PR) and derivatives thereof, suggesting use of these compounds in the treatment of amyloid-associated diseases.

As is illustrated in the Examples section which follows, aromatic compounds of the present invention such as phenol red and derivatives thereof (e.g., diacetoxy phenol red and dimethoxy phenol red), green tea polyphenols, and pyrocatechol violet efficiently inhibited aggregation of an amyloid peptide (hIAPP$_{22-29}$) as determined by a number of biochemical and ultra-structural morphology analyses. In line with this, a remarkable inhibition in hIAPP$_{1-37}$ fibril cytotoxicity towards pancreatic β cells was evident in the presence of phenol red (see, Examples 8-9 of the Examples section which follows), rendering the aromatic compounds of the present invention promising tools for treating amyloid associated diseases, such as Type II diabetes mellitus.

Thus, the present invention provides a method of treating an amyloid-associated disease in a subject.

Preferred individual subjects according to the present invention are mammals such as canines, felines, ovines, porcines, equines, and bovines. Preferably the individual subjects according to the present invention are humans.

The term "treating" refers to reducing or preventing amyloid plaque formation, or substantially decreasing plaque occurrence in an affected tissue. The phrase "amyloid plaque" refers to fibrillar amyloid as well as aggregated but not fibrillar amyloid, hereinafter "protofibrillar amyloid", which may be pathogenic as well [see Anaguiano et al. (2002) Biochemistry 41:11338-43].

Amyloid-associated diseases treated according to the present invention include, but are not limited to, type II diabetes mellitus, Alzheimer's disease (AD), early onset Alzheimer's disease, late onset Alzheimer's disease, presymptomatic Alzheimer's disease, Parkinson's disease, SAA amyloidosis, hereditary Icelandic syndrome, multiple myeloma, medullary carcinoma, aortic medical carcinoma, Insulin injection amyloidosis, prion-systematic amyloidosis, choronic inflammation amyloidosis, Huntington's disease, senile systemic amyloidosis, pituitary gland amyloidosis, Hereditary renal amyloidosis, familial British dementia, Finnish hereditary amyloidosis, familial non-neuropathic amyloidosis [Gazit (2002) Curr. Med. Chem. 9:1667-1675] and prion diseases including scrapie of sheep and goats and bovine spongiform encephalopathy (BSE) of cattle [Wilesmith and Wells (1991) Curr Top Microbiol Immunol 172: 21-38] and human prion diseases including (i) kuru, (ii) Creutzfeldt-Jakob Disease (CJD), (iii) Gerstmann-Streussler-Sheinker Disease (GSS), and (iv) fatal familial insomnia (FFI) [Gajdusek (1977) Science 197: 943-960; Medori, Tritschler et al. (1992) N Engl J Med 326: 444-449].

The method, according to the present invention, is effected by administering to a subject in need thereof, a therapeutically effective amount of a compound having the general Formula I:

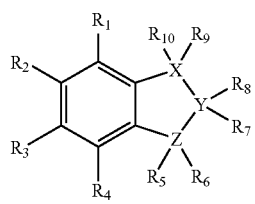

Formula I a pharmaceutically acceptable salt thereof or a prodrug thereof, wherein:

X, Y and Z are each independently selected from the group consisting of carbon, oxygen, sulfur, $CR_{11}R_{12}$ or $R_{13}R_{14}C$—$CR_{15}R_{16}$, provided that at least one of X, Y and Z is oxygen or sulfur;

$R_1$—$R_{16}$ are each independently selected from the group consisting of hydrogen, lone pair electrons, hydroxy, alkyl, cycloalkyl, phenyl, alkoxyphenyl, thioalkoxyphenyl, aryloxyphenyl, thioaryloxyphenyl, carboxyphenyl, thiocarboxyphenyl, phenol, hydroxyphenol, dihydroxyphenol, aryl, alkenyl, alkynyl, heteroaryl, heteroalicyclic, halo, alkoxy, aryloxy, thiohydroxy, thioalkoxy, thioaryloxy, C-carboxy, O-carboxy, thiocarboxy, carbonyl, oxo, thiocarbonyl, sulfinyl, and sulfonyl, or absent, or, alternatively, at least two of $R_1$—$R_4$ and/or at least two of $R_5$—$R_{16}$ form at least one five- or six-membered aromatic, heteroaromatic, alicyclic or heteroalicyclic ring, whereas:

at least one of $R_1$—$R_4$ is selected from the group consisting of hydroxy, alkoxy, aryloxy, thiohydroxy, thioalkoxy, thioaryloxy, O-carboxy and O-thiocarboxy; and/or at least one of $R_5$—$R_{16}$ comprises phenol, alkoxyphenyl, thioalkoxyphenyl, aryloxyphenyl, thioaryloxyphenyl, carboxyphenyl, thiocarboxyphenyl hydroxyphenol, and dihydroxyphenol.

Excluded from the scope of the present invention are compounds having Formula I above, in which X is carbon, Y is $R_{13}R_{14}C$—$CR_{15}R_{16}$, and Z is carbon or sulfur.

The compounds according to the present invention therefore include at least one phenol moiety (preferably at least two phenol moieties). As is further defined hereinbelow, each of the phenol moieties can be either unsubstituted or substituted, preferably by one or more hydroxy groups, thus being hydroxyphenol or dihydroxyphenol. Each of the phenol moieties can be present within the compounds of the present invention either per se, namely as a hydroxyphenyl moiety, or as an alkoxylated or carboxylated phenol moiety, namely, as an alkoxyphenyl or carboxyphenyl moiety, as is delineated hereinunder.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined hereinbelow.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined hereinbelow.

A "hydroxy" group refers to an —OH group.

An "alkenyl" group refers to an alkyl group, as defined hereinabove, which consists of at least two carbon atoms and at least one carbon-carbon double bond.

An "alkynyl" group refers to an alkyl group, as defined hereinabove, which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A preferred example of a substituted aryl, according to the present invention is phenol.

As used herein, the term "phenol" refers to a phenyl substituted by an hydroxy group. The phenol group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A preferred example of a substituted phenol, according to the present invention, is hydroxyphenol.

As used herein, the term "hydroxyphenol", which also encompasses the term "dihydroxyphenol" refers to a phenol, as defined hereinabove, which is further substituted by one or more additional hydroxy groups. The additional hydroxy groups can be at the para, ortho and/or meta positions with respect to the hydroxy group of the phenol. The hydroxyphenol may be additionally substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl,-N-carbamyl,-O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

Another preferred examples of a substituted aryl, according to the present invention, include alkoxyphenyl, thioalkoxyphenyl, aryloxyphenyl and thioaryloxyphenyl.

As used herein, the term "alkoxyphenyl" refers to a phenyl substituted by an alkoxy group, as defined herein. A representative example of an alkoxy group is methoxy.

The term "thioalkoxyphenyl" refers to a phenyl substituted by a thioalkoxy group, as defined herein.

The term "aryloxyphenyl" refers to a phenyl substituted by an aryloxy group, as defined herein.

The term "thioaryloxyphenyl" refers to a phenyl substituted by a thioaryloxy group, as defined herein.

Each of the alkoxyphenyl, thioalkoxyphenyl, aryloxyphenyl and thioaryloxyphenyl groups may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

Preferred substituents of the alkoxyphenyl, thioalkoxyphenyl, aryloxyphenyl and thioaryloxyphenyl groups include alkoxy, thioalkoxy, aryloxy and/or thioaryloxy groups, such that examples of preferred substituted alkoxyphenyl, thioalkoxyphenyl, aryloxyphenyl and thioaryloxyphenyl include dialkoxyphenyl, dithioalkoxyphenyl, diaryloxyphenyl and dithioaryloxyphenyl, and any other combination.

As used herein, the term "dialkoxyphenyl", refers to an alkoxyphenyl, as defined hereinabove, which is further substituted by one or more additional alkoxy groups. The additional alkoxy groups can be at the para, ortho and/or meta positions with respect to the alkoxy group of the alkoxyphenyl.

The term "dithioalkoxyphenyl", refers to a thioalkoxyphenyl, as defined hereinabove, which is further substituted by one or more additional thioalkoxy groups. The additional thioalkoxy groups can be at the para, ortho and/or meta positions with respect to the thioalkoxy group of the thioalkoxyphenyl.

The term "diaryloxyphenyl", refers to an aryloxyphenyl, as defined hereinabove, which is further substituted by one or more additional aryloxy groups. The additional aryloxy groups can be at the para, ortho and/or meta positions with respect to the aryloxy group of the aryloxyphenyl.

The term "dithioaryloxyphenyl", refers to a thioaryloxyphenyl, as defined hereinabove, which is further substituted by one or more additional thioaryloxy groups. The additional thioaryloxy groups can be at the para, ortho and/or meta positions with respect to the thioaryloxy group of the thioaryloxyphenyl.

Each of the dialkoxyphenyl, dithioalkoxyphenyl, diaryloxyphenyl and dithioaryloxyphenyl may be additionally substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

Another preferred examples of a substituted aryl, according to the present invention, include carboxyphenyl and thiocarboxyphenyl.

As used herein, the term "carboxyphenyl" refers to a phenyl substituted by an O-carboxy group, as defined herein. A representative example of an O-carboxy group is O-acetoxy.

The term "thiocarboxyphenyl" refers to a phenyl substituted by a thiocarboxy group, as defined herein.

The carboxyphenyl and the thiocarboxyphenyl may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

Preferred substituents include additional O-carboxy or thiocarboxy groups, such that examples of preferred substituted carboxyphenyl and thiocarboxyphenyl include dicarboxyphenyl and dithiocarboxyphenyl.

As used herein, the term "dicarboxyphenyl", refers to a carboxyphenyl, e.g., acetoxyphenyl, as defined hereinabove, which is further substituted by one or more additional carboxy groups. The additional carboxy groups can be at the para, ortho and/or meta positions with respect to the carboxy group of the carboxyphenyl.

The term "dithiocarboxyphenyl", refers to a thiocarboxyphenyl, as defined hereinabove, which is further substituted by one or more additional thiocarboxy groups. The additional thiocarboxy groups can be at the para, ortho and/or meta positions with respect to the thiocarboxy group of the thiocarboxyphenyl.

Each of the dicarboxyphenyl and dithiocarboxyphenyl may be additionally substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein. Representative examples are piperidine, piperazine, tetrahydrofurane, tetrahydropyrane, morpholino and the like.

A "halo" group refers to fluorine, chlorine, bromine or iodine.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

An "thioaryloxy" group refers to both an —S-aryl and an —S-heteroaryl group, as defined herein.

An "oxo" group refers to an =O group.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

A "C-carboxy" group refers to a —C(=O)—O—R' groups, where R' is as defined herein.

An "O-carboxy" group refers to a R"C(=O)—O— group, where R" is as defined herein.

A "thiocarboxy" group refers to a R"C(=O)—S— group, where R" is as defined herein.

A "sulfinyl" group refers to an —S(=O)—R" group, where R" is as defined herein.

A "sulfonyl" group refers to an —S(=O)$_2$—R' group, where R" is as defined herein.

A "trihalomethyl" group refers to a —CX group wherein X is a halo group as defined herein.

A "trihalomethanesulfonyl" group refers to a $X_3$CS(=O)$_2$— group wherein X is a halo group as defined herein.

A "S-sulfonamido" group refers to a —S(=O)$_2$—NR'R" group, with R' and R" as defined herein.

A "N-sulfonamido" group refers to n R'S(=O)$_2$—NR" group, where R' and R" are as defined herein.

A "trihalomethanesulfonamido" group refers to an $X_3$CS(=O)$_2$NR'— group, where R' and X are as defined herein.

An "O-carbamyl" group refers to an —OC(=O)—NR'R" group, where R' and R" are as defined herein.

An "N-carbamyl" group refers to an R"OC(=O)—NR'— group, where R' and R" are as defined herein.

An "O-thiocarbamyl" group refers to an —OC(=S)—NR'R" group, where R' and R" are as defined herein.

An "N-thiocarbamyl" group refers to an R"OC(=S)NR'— group, where R' and R" are as defined herein.

An "amino" group refers to an —NR'R" group where R' and R" are as defined herein.

A "C-amido" group refers to a —C(=O)—NR'R" group, where R' and R" are as defined herein.

An "N-amido" group refers to an R'C(=O)—NR" group, where R' and R" are as defined herein.

An "urea" group refers to an —NR'C(=O)—NR"R'" group, where R' and R" are as defined herein and R'" is defined as either R' or R".

A "guanidino" group refers to an —R'NC(=N)—NR"R'" group, where R' , R" and R'" are as defined herein.

A "guanyl" group refers to an R'R"NC(=N)— group, where R' and R" are as defined herein.

A "nitro" group refers to an —NO$_2$ group.

A "cyano" group refers to a —C≡N group.

An "azo" group refers to a —N=N group.

The term "phosphonyl" describes a —O—P(=O)(OR') (OR") group, with R' and R" as defined hereinabove.

The term "phosphinyl" describes a —PR'R" group, with R' and R" as defined hereinabove.

Preferred compounds according to the present invention therefore include, for example, phenol red and analogs thereof, such that in the Formula above X is carbon; Y is oxygen; Z is carbon or sulfur; and at least one of $R_5$ and $R_6$ is oxo, as this term is defined hereinabove. Such compounds include a heteroalicyclic ring, fused with phenyl, and further substituted by one or more phenol or phenyl groups, such that at least one of $R_5$—$R_{10}$ is phenol or hydroxyphenol, as defined hereinabove. Such compounds in which at least one, and preferably two, of $R_5$—$R_{10}$ are hydroxyphenol include, for example, pyrocatechol violet and analogs thereof.

Compounds in this category, in which Z is sulfur, are typically phenol red analogs, whereas compounds in which Z is carbon are typically phenolphthaleine analogs. The chemical structures of phenol red, pyrocatechol violet and phenolphthalein are depicted in FIG. 7.

Additional compounds are those having the Formula above, in which X is carbon; Y is $R_{13}R_{14}C-CR_{15}R_{16}$; and Z is oxygen. Such compounds therefore include a tetrahydropyrane ring fused to phenyl.

Examples of compounds in this category include analogs and derivatives of catechins such as, for example, analogs and derivatives of epicatechin, epigallocatechin, epigallocatechin gallate and the like, all include two hydroxy group at the $R_1$ and $R_3$ positions and a hydroxyphenol or dihydroxyphenol group, directly or indirectly attached to the tetrahydropyrane ring, at one or more of the $R_{13}-R_{16}$ positions in the Formula above.

As is shown in the Examples section that follows, catechin gallates, which include an additional phenol moiety, were found to be highly potent inhibitors, thus indicating an important role of the number of the phenyl moieties in the compound.

Additional preferred examples of these compounds include an oxidized tetrahydropyrane ring fused to a phenyl, such that $R_9$ is oxo; and $R_{10}$ is absent.

Further additional preferred compounds in this category include tocopherol and analogs thereof, which include one or more alkyl groups at the $R_{13}-R_{16}$ positions, whereby the alkyl groups can include lower alkyls (e.g., methyl) and/or alkyls having more than 8 carbon atoms.

Further according to the present invention, each of the compounds described above can further be in a dimeric form. Such a dimeric form includes two moieties having the Formula above, attached therebetween via $R_1-R_{16}$, directly or indirectly.

Examples of compounds which can be used in accordance with the present invention therefore include, but are not limited to, phenol red, pyrocatechol violet, phenolphthaleine, catechin, epigallocatechin gallate, epicatechin gallate, epicatechin, epigallocatechin, eriodictyol, quercetin, procyanidin, hydroxyphenyl, tocopherol, bromophenol red, analogs thereof, derivatives thereof and any combination thereof.

The presently most preferred compounds according to the present invention are phenol red, and pyrocatechol violet.

However, additional preferred compounds which can be used in accordance with the present invention include the mono-, di-, tri- and tetra-alkoxy (e.g., methoxy) or carboxy (e.g., acetoxy) derivatives of the compounds listed above. Such derivatives are meant to include compounds in which one or more of the hydroxy groups in the phenol or hydroxyphenol moieties are derivatized by, e.g., an alkyl or acyl group, resulting, for example, in an alkoxyphenyl moiety, a dialkoxyphenyl moiety, a carboxyphenyl moiety or a di-carboxyphenyl moiety.

Representative examples of such derivatives include, but are not limited to, methoxy phenol red and acetoxy phenol red, in which one phenol moiety in phenol red is replaced by a methoxyphenyl or an acetoxyphenyl moiety, respectively, and dimethoxy phenol red (also referred to herein as PF4) and diacetoxy phenol red (also referred to herein as PF3), in which the two phenol moieties in phenol red are -replaced by two methoxyphenyl or acetoxyphenyl moieties, respectively. The chemical structures of PF3 and PF4 are presented in FIG. 7. The presently most preferred phenol red derivative is diacetoxy phenol red (PF3).

Such a derivatization of the hydroxy groups, which results in the replacement of one or more of the phenol moieties by an alkoxyphenyl moiety, a dialkoxyphenyl moiety, a carboxyphenyl moiety or a di-carboxyphenyl moiety, as well as analogs thereof (e.g., aryloxyphenyl, thioalkoxyphenyl, and the like, as is detailed hereinabove) is highly advantageous since it reduces the hydrophilic nature of the compounds and thus enhances their absorption in the intestines.

As is well known in the art, hydrophilic compounds are typically characterized by relatively low absorption due to poor permeability across human intestinal epithelial. Due to these low absorption parameters, treatment with hydrophilic compounds requires the administration of high doses, when administered orally. Hence, reducing the hydrophilic nature of the compounds described above provides for enhanced absorption thereof, particularly in the intestines, and enables an effective oral administration thereof. The effect of reducing the hydrophilic nature of compounds on their absorption was clearly shown in several models, including the Caco-2 cells and parallel artificial membrane permeation assay (PAMPA). These studies demonstrated that increased hydrophobiciy significantly improves the permeability of small organic compounds [Ano (2004) Bioorg Med Chem. 12:257-264; Ano (2004) 12: 249-255].

The poor bioavailability of phenol red has been widely recognized in the art. In fact, phenol red is often utilized in intestinal absorption studies as a non-absorbable marker (see, for example, Drug Metab Pharmacokinet. (2004) June;19(3): 198-205; Drug Metab Dispos. (2000) May;28(5):577-81).

As is demonstrated in the Examples section that follows (see, Example 10), studies conducted for CaCo-2 transport of phenol red derivatives indicated, for example, that the diacetoxy phenol red derivative (PF3) indeed transports through CaCo-2 monolayer, indicating its permeability across intestinal membranes and hence demonstrating its efficacy upon oral administration. Additional studies (see, Example 12) have shown that PF3, when orally or intravenously administered to mice, acts as a prodrug, producing phenol red upon in vivo hydrolysis of the acetoxy groups. PF3 was found to have a substantially improved bioavilability as compared with phenol red.

Of a particular importance are the mono derivatives of phenol red, namely, methoxy phenol red and acetoxy phenol red and analogs thereof. These mono derivatives simultaneously provide for (i) enhanced inhibition activity due to the presence of hydroxy groups; (ii) enhanced oral bioavailability due a partial hydrophilic nature thereof; and (iii) enhanced absorption due to a partial hydrophobic nature thereof, as is detailed hereinabove.

The effect of the hydroxy groups on the inhibition activity of the compounds is demonstrated in the Examples section that follows (see, for example, Example 5). The effect of the hydrophilic nature of compounds on oral bioavailability is well known in the art, (as is demonstrated, for example, in Hite et al. (2003) Part 1. Oral Delivery of Poorly Soluble Drugs. PMPS Summer pp: 38-40) and is further demonstrated in the Exampels section that follows (see, for example, Example 10).

Hence, the phenol red mono derivatives of the present invention, by combining enhanced inhibition activity, enhanced oral bioavailability and enhanced absorption, are highly advantageous.

Although some phenol red derivatives, in which the two hydroxy groups are derivatized by alkyl or acyl groups, are known, these compounds have never been used for inhibiting amyloid fibril formation. Furthermore, the selective synthesis of the mono derivatives of phenol red mentioned above has never been practiced hitherto.

Hence, according to another aspect of the present invention, there are provided novel phenol red derivatives having the general formula II as follows:

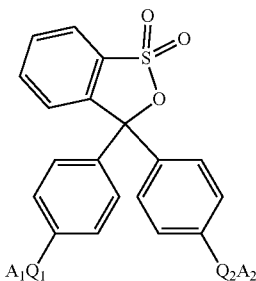

Formula II wherein:

$Q_1$ and $Q_2$ are each independently selected from the group consisting of oxygen and sulfur; and $A_1$ and $A_2$ are each independently selected from the group consisting of hydrogen, alkyl, aryl, cycloalkyl and carbonyl, whereby when $Q_1$ and $Q_2$ are each oxygen, one of $A_1$ and $A_2$ is hydrogen and the other is selected from the group consisting of alkyl, cycloalkyl and aryl.

These phenol red derivatives therefore include, for example, methoxy phenol red, in which $Q_1$ and $Q_2$ are each oxygen, one of $A_1$ and $A_2$ is hydrogen and the other is alkyl, preferably methyl, and acetoxy phenol red, in which $Q_1$ and $Q_2$ are each oxygen, one of $A_1$ and $A_2$ is hydrogen and the other is carbonyl, preferably acetyl (a $C(\!\!=\!\!O)CH_3$ group).

The compounds described above can be administered or otherwise utilized in this and other aspects of the present invention, either as is or as a pharmaceutically acceptable salt or a prodrug thereof.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more phenol moieties, which is administered as an ester (the "prodrug", e.g., as a carboxyphenol). Such a prodrug is hydrolysed in vivo, to thereby provide the free compound (the parent drug). The selected ester may affect both the solubility characteristics and the hydrolysis rate of the prodrug.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a phenolic anion and a cation such as, but not limited to, ammonium, sodium, potassium and the like.

The compounds described above can further be utilized or administered as hydrates, namely, as a complex of variable stoichiometry (e.g., di-, tri-, tetra-, penta-, hexa-, and so on) formed between the compound and water molecule(s).

Preferably, the compound of the present invention is administered at a concentration not exceeding 4 mg/Kg×hr.

The compounds of the present invention can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to the subject treated.

Herein the term "active ingredient" refers to the compound, which is accountable for the biological effect.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered compound.

Preferred carriers of the pharmaceutical composition of the present invention include, but are not limited to, polyethylene glycol (PEG), a biocompatible polymer with a wide range of solubility in both organic and aqueous media (Mutter et al. (1979).

An exemplary preferred carrier which was found highly suitable for use with diacetoxy phenol red (PF3) is a mixture of polyethylene glycol (e.g., PEG 400), N,N-dimethylacetamide and a saturated sodium chloride (saline). Such a carrier was found highly suitable for use in pharmaceutical compositions that are formulated for both oral and intravenous administration (see, for example, Examples 11 and 12 in the Exampels section that follows). Additional examples of carriers that are usable in this context of the present invention are also delineated in the Examples section that follows (see, Example 11).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable. propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that treatment of amyloid-associated diseases according to the present invention may be combined with other treatment methods known in the art (i.e., combination therapy). Thus, compounds of the present invention may be co-administered (simultaneously or separately) with additional anti-amyloid drugs. Examples of such anti-amyloid drugs include, but are not limited to, amyloid-destabilizing antibodies, amyloid-destabilizing peptides and anti-amyloid small molecules (further details on such drugs are provided in the preceding Background section).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York. (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Peptide Synthesis:
Peptide synthesis using solid-phase methods was performed by Peptron, Inc. (Taejeon, Korea) for hIAPP$_{22-29}$ (SEQ ID NO: 1) and for hIAPP$_{20-29}$ (SEQ ID NO: 2), and by Calbiochem (CalBiochem Calif., USA) for hIAPP$_{1-37}$ (SEQ ID NO: 3). The identity of the peptides was confirmed by ion spray mass-spectrometry and the purity of the peptides was confirmed by reverse phase high-pressure liquid chromatography (RP-HPLC). The stock solution for hIAPP$_{22-29}$ and hIAPP$_{20-29}$ were prepared by dissolving lyophilized form of the peptides in Me$_2$SO (DMSO) at a concentration of 50 mM. The stock solution for hIAPP$_{1-37}$ was prepared by dissolving lyophilized form of the peptide in 3,3,3,3',3',3'-hexafluoro-2-propanol (HFIP) at a concentration of 400 μM. To avoid any pre-aggregation the stock solution was sonicated for 2 min before each experiment.

Materials:
Phenol red was purchased from Sigma (Rehovot, Israel).
Pyrocatechol violet was purchased from Riedel-de Haën (Seelze, Germany).
Diacetoxy phenol red (PF3) and dimethoxy phenol red (PF4) were synthesized by TAMI institute for Research & Development Ltd. (Haifa, Israel).
Epigallocatechin gallate, Gallocatechin gallate, Gallocatechin, Epigallocatechin, Catechin and Congo red were purchased from SIGMA (Rehovot, Israel).
Epicatechin gallate and Epicatechin were purchased from ICN Biomedicals.
N,N-Dimethylacetamide (DMA) was purchased from Merck (Cat. No. 8.03235.1000).
Polyethylene glycol (PEG) 400 was purchased from Merck (Cat. No. 1.59710.0050).
Water for injection, BP grade, were obtained from B. Braun (USA).
Sodium chloride solution (saline) was purchased from Teva Medical (Cat. No. AWB1324).
Hydroxypropyl β-cyclodextrin (HPBCD) was purchased from Pharmaceutical grade.
Cavitron 82005 was purchased from Pharmaceutical grade.
Carboxy methyl cellulose (CMC), TWEEN80 and corn oil were purchased from Sigma (Rehovot, Israel).
Acetonitrile HPLC grade was purchased from Baker (Cat. No. 9017).
Water HPLC grade was purchased from Baker (Cat. No. 42180).
Trifluoroacetic acid (TFA) HPLC grade was purchased from Baker (Cat. No. 9470).

Kinetic Aggregation Assay:
Stock solutions of hIAPP$_{22-29}$ and hIAPP$_{20-29}$ peptide were prepared by dilution of lyophilized peptides into 10 mM Tris-HCl (pH 7.2) buffer to a final concentration of 1 mM peptide and 4% DMSO. Turbidity data were collected at 405 or 560 nm at room temperature. A buffer solution containing the same amount of DMSO as the tested samples was used as blank. Turbidity was measured using disposable UVette cuvettes (Eppendorf, Germany) and a Scinco S-3100 spectrophotometer.

Thioflavin T Fluorescence Assay:

Fibrillization of hIAPP$_{1-37}$ was monitored by Thioflavin T dye binding assay. hIAPP$_{1-37}$ stock solution was diluted to a final concentration of 4 µM in 10 mM sodium acetate buffer (pH 6.5) with or without inhibitor, and a final HFIP concentration of 1% (vol). Immediately after dilution, sample was centrifuged for 20 minutes in 20,000 g at 4° C. and the supernatant fraction was used for the fluorescence measurements. In every measurement ThT was added to a final concentration of 3 µM and measurements were carried out using Perkin Elmer (excitation 450 nm, 2.5 nm slit; emission 480 nm 10 nm slit). For the phenol red concentration dependent inhibition experiments, samples were diluted 10 fold such that maximal phenol red concentration did not exceed 4 µM, and measured using Jobin Yvon Horiba Fluoromax 3 fluorimeter (excitation 450 nm, 2.5 run slit; emission 482 nm, 5 nm slit). Background was subtracted from all samples.

Circular Dichroism Spectroscopy:

To follow secondary structure formation, hIAPP$_{1-37}$ (4 µM) was prepared as mentioned above, with or without inhibitor (40 µM). Spectra were recorded at 25° C. between 200-250 nm, with 1 nm intervals and 4 sec averaging time, using an AVIV 202 CD spectrometer. Final scan values represent subtraction of base line (buffer in case of hIAPP, and buffer with phenol red for the inhibition assay) and smoothing using AVIV CDS version 2.73 software.

Transmission Electron Microscopy:

10 µL samples of hIAPP$_{22-29}$ or hIAPP$_{20-29}$ from the aggregation assay, and hIAPP$_{1-37}$ from the fluorescence assay were placed on 400-mesh copper grids (SPI supplies, West Chester Pa.) covered by carbon-stabilized Formvar film. After 1 minute, excess fluid was removed, and the grids were negatively stained with 2% uranyl acetate in water for another two minutes. Samples were viewed in a JEOL 1200EX electron microscope operating at 80 kV.

MTT Assay:

βTC-tet cells [Fleischer, N., Chen C., Surana, M., Leiser, M., Rossetti, L., Pralong, W. and Efrat, S. (1998) Functional analysis of a conditionally transformed pancreatic beta-cell line, *Diabetes* 47, 1419-1425] or PC12 cells (ATCC # CRL-1721) were plated on 24-well plates (2-10$^5$/well) or on 96-well plates (1-10$^4$/well) respectively, and allowed to adhere for 24 hours. Synthetic hIAPP$_{1-37}$ stock solution was diluted to a final concentration of 4 µM in serum free growth medium [Fleischer (1998) Supra] containing DMEM with or without phenol red. Immediately following dilution, samples were centrifuged at 4° C. for 20 minutes at 20,000 g, and the supernatant was bubbled with nitrogen for 30 min to evaporate residual HFIP. Cells were washed twice with PBS and incubated with the supernatant for 24 hrs. MTT (Sigma M-2128) was then added for 3 hrs, followed by addition of lysis buffer and incubation over night. Assay was effected according to Manufacturer's instructions. Samples were read at 570 nm. Cell viability was calculated in comparison to cells incubated in the absence of hIAPP in medium with or without phenol red, respectively.

Scanning Electron Microscopy:

Cells were grown on glass microscope cover slips under the same conditions as for the MT assay. Immediately following incubation with hIAPP, the cells were fixed with 2% glutaraldehide (v/v) and stored for 24 hrs at 4° C. The cells were serially dehydrated with increasing concentrations of ethanol (30%, 50%, 70%, 90%, 95%, 100%) and dried with a critical point drier. Specimen cover slips were coated with colloidal gold and viewed using a JOEL JSM 840A microscope operating at 25 kV.

Example 1

Effect of Phenol Red on the Aggregation of the Core Amyloidogenic Fragments of hIAPP The core amyloidogenic fragments of hIAPP (hIAPP$_{22-29}$, hIAPP$_{20-29}$) aggregate in an aqueous solution. Such an aggregation behavior was served as a preliminary assay for amyloid formation.

In order to evaluate the ability of phenol red to inhibit amyloid formation, the aggregation of 1 mM hIAPP$_{22-29}$ and hIAPP$_{20-29}$ (SEQ ID NO: 1 and NO: 2, respectively) was examined in the absence or presence of 40 mM phenol red. To verify the specificity of phenol red molecule towards hIAPP core peptides, a very similar molecule—phenolphthaleine, which differs only by the lack of the sulfon group, was used as control (FIG. 7).

As shown in FIGS. 1*a-b*, hIAPP$_{20-29}$ aggregation rate was lower than hIAPP$_{22-29}$, and approximately two hours lag time was evident in all samples. No inhibition effect was evident using phenolphthaleine and its aggregation curve was similar to hIAPP$_{20-29}$ aggregation which increased dramatically after three hours (FIG. 1*b*). Using phenol red as an inhibitor decreased aggregation showing very minor elevation in aggregation levels after 3 hours of incubation.

As is shown in FIG. 1*a*, hIAPP$_{22-29}$ aggregated within seconds and its turbidity reached a plateau following 10 minutes of incubation. However, in the presence of phenol red, aggregation of hIAPP$_{22-29}$ was substantially terminated exhibiting much lower rate and constant levels of turbidity.

EXAMPLE 2

Secondary Structure Evaluation Using Circular Dichroism (CD)

Wild type hIAPP$_{1-37}$ (SEQ ID NO: 3) undergoes a transition from random coil conformation to β sheet within the fibrillization process. This secondary structure transition was addressed in the presence or absence of phenol red. hIAPP$_{1-37}$ was dissolved in HFIP and diluted into sodium acetate buffer (pH 6.5) to a final concentration of 4 µM and 1% HFIP. Changes in the peptide secondary structure were monitored for 96 hours.

As shown in FIG. 2*a*, in the absence of phenol red, hIAPP$_{1-37}$ showed an initial transition to β sheet structure within 6 hours and maximal ellipticity (218 nm, which corresponds to β sheet structures) within 24 hours. These structures remained relatively steady for 96 hours.

Upon the addition of 10 molar ratio of phenol red, transition to β sheet conformation was significantly inhibited (FIG. 2*b*), wherein initial very low levels of 218 nm ellipticity were measured after 46 hours with very slow enhancement after 96 hours.

EXAMPLE 3

Amyloid Fibril Formation by Thioflavin T Fluorescence

Thioflavin T (ThT) is commonly used for detecting the level of amyloid formation. hIAPP$_{1-37}$ solution was prepared as described above. Following incubation in the presence or absence of phenol red and addition of 3 μM ThT to each sample, fluorescence was measured.

As is shown in FIG. 3a, in the absence of phenol red, hIAPP$_{1-37}$ displayed a lag phase of approximately 20 hours that was followed by a fast enhancement in fluorescent levels. In the presence of 40 μM phenol red, very low and constant levels of fluorescence were detected for throughout the assay. A dose dependent inhibitory effect of phenol red on aggregation of the hIAPP peptide is shown in FIGS. 3b-c. Higher phenol red concentrations (higher than 4 fold of phenol red to hIAPP) have shown constant low fluorescence levels following 24 hours (FIG. 3b). Even after one week of incubation, the concentration dependent inhibition was similar (FIG. 3c), and inhibition level of about 90% was achieved for phenol red concentration of 20 μM and above. These results substantiate that phenol red is a potent inhibitor of amyloid fibril formation.

EXAMPLE 4

Morphology of hIAPP Fibrils with Phenol Red as Determined by TEM

Samples of hIAPP$_{22-29}$ and hIAPP$_{20-29}$ taken from the aggregation assay (described in Example 3) were visualized using transmission electron microscopy. As is shown in FIG. 4a, distinct and well-defined amyloid fibers were observed 3 and 72 hours after initiation of aggregation in both samples of the hIAPP$_{22-29}$ peptide, with a minor increase in fiber density and width following 72 hours. In contrast, in the presence of phenol red, no fibers were visualized following 3 hours while only small amount of fibrils, with different morphology were visualized after 72 hours. Same results were obtained with the hIAPP$_{20-29}$ peptide after 24 hr incubation (FIG. 4b) in the presence of phenol red inhibitor. No inhibition was observed using phenolphthaleine under the same conditions and fibrillar structures were evident on the TEM grid.

As is shown in FIG. 4c, the same inhibitory tendency was observed when using phenol red as an inhibitor of hIAPP$_{1-37}$ amyloidosis. A significant kinetic inhibition in fiber formation was present in the first stage of fiber formation (approximately 30 hours) where no fibers where present in presence of phenol red.

EXAMPLE 5

Inhibition of IAPP Fibril Formation with Green Tea Polyphenols

ThT was used to determine the inhibitory effect of green tea polyphenol compounds on hIAPP$_{1-37}$ fibril formation (See Example 3).

As is shown in FIG. 5a, all polyphenol compounds had a long-term inhibitory effect on hIAPP$_{1-37}$ fibril formation as compared to the hIAPP alone. This inhibition resembled the inhibitory effect of congo red. Fluorescence values of LAPP alone increased after 48 hr while an initial increase of hIAPP$_{1-37}$ fluorescence in the presence of inhibitors was detectable only after 72 hr.

A more detailed observation of the inhibitory effect revealed that all poly phenols with the gallate group (i.e., containing an additional phenolic ring) are better inhibitors (FIG. 5b). This may suggest that there is an importance to the additional aromatic ring on the inhibitory effect. This result was independently confirmed by two other groups [Lashuel et al *J. Biol. Chem.* 2002 277:42881-90; Kocisco et al *J. Virol.* 2004 77: 10288-10294] describing the inhibitory effect of Apomorphines on β-amyloid and the inhibitory effect of various polyphenols on scrapie-associated prion protein.

EXAMPLE 6

Dose-Dependent Inhibition of Human Islet Amyloid Polypeptide Fibril Formation by Pyrocatechol Violet Fibrillization of hIAPP$_{1-37}$ was monitored by Thioflavin T (ThT) dye binding assay, as described above, using an inhibitor concentration of 40 μM or 4 μM.

As is shown in FIG. 6, the results obtained in the ThT assay clearly show that pyrocatechol violet effectively inhibit amyloid formation by hIAPP$_{1-37}$. While hIAPP without pyrocatechol violet displayed a quick increase in fluorescence levels, as demonstrated by a peak value already at the first time point (2.6 hours), addition of 4 μM pyrocatechol violet resulted in a significant lower level of fluorescence throughout the entire assay, whereby an even stronger inhibitory effect was detected upon addition of 40 μM pyrocatechol violet.

EXAMPLE 7

Inhibition of IAPP Fibril Formation by Phenol Red Derivates

To evaluate the ability of the phenol red derivatives described hereinabove PF3 (diacetoxy phenol red, FIG. 7) and PF4 (dimethoxy phenol red, FIG. 7) to inhibit fibril formation as compared to phenol red, a fluorescence ThT kinetic assay was effected.

As is evident from FIGS. 8a-b, both PF3 and PF4 (40 μM) molecules have exhibited reduced inhibition effect relatively to the phenol red molecule. PF3 molecule was found not stable and tended to fragmentize within few minutes of solubilization. PF4 molecule relative inhibitory effect was more evident, especially when the sample was not centrifuged (FIG. 8b).

EXAMPLE 8

Effect of Phenol Red on the Survival of PC12 Cells Treated with hIAPP

To study the effect of phenol red on cytotoxicity induced by hIAPP$_{1-37}$ aggregates, the PC12 cell line was used. Cells were grown in a 96 well plate with or without gradual concentration of phenol red, while adding fresh hIAPP$_{1-37}$ to the growth medium. Following 24 hours incubation, cell viability was calculated by substitution of LAPP samples absorbance with non IAPP controls containing the same phenol red concentrations. As is evident from FIG. 9, the MTT cell viability assay showed concentration dependent rescue of the cells by phenol red.

EXAMPLE 9

Effect of Phenol Red on the Cytotoxic Effect of Amyloid Aggregates in Pancreatic β Cells The ability of phenol red to modulate cytotoxicity effect of hIAPP amyloid assemblies on pancreatic β cells in culture was addressed. A highly-differentiated murine β-cell line (βTC-tet, Fleischer 1998 SUpra) with a normal insulin secretory response to glucose was used. Cells were grown with or without phenol red, and fresh hIAPP was added to the growth medium. An MTT cell viability assay clearly revealed that the presence of phenol red in the medium protected β cells from the cytotoxic effect of hIAPP assemblies and increased cell viability from 50% to 80% (P<0.05) (FIG. 10a). Scanning electron microscopy (SEM) analysis of β cells that were grown in the presence of hIAPP showed an extensive membrane blebbing (FIG. 10b), as previously reported for hIAPP cytotoxicity [Saafi, E. L., Konarkowska, B., Zhang, S., Kistler, J. and Cooper, G. J. (2001) Ultrastructural evidence that apoptosis is the mechanism by which human amylin evokes death in RINm5F pancreatic islet beta-cells, *Cell. Biol. Int.* 25, 339-350], and a collapse of typical cellular morphology in the vast majority of cells (FIG. 10d). On the other hand, practically no significant difference could be observed between untreated cells (FIG. 10h) and cells grown in the presence of hIAPP and phenol red (FIG. 10f). In both cases, most of the cells maintained normal morphology. No blebbing was visible, and membrane extensions of microspikes and lamellipodia were present. Furthermore, at low magnification SEM examination, normal arrays of □-cells could be observed with the phenol red protected cells and control cells (FIGS. 10e and 10g, respectively). In marked contrast, only isolated and morphologically altered cells could be observed upon LAPP incubation with no phenol red protection (FIG. 10c).

Taken together these results indicate that phenol red inhibits the cytotoxic effect of $hIAPP_{1-37}$ fibrils on cells, particularly pancreatic β cells.

EXAMPLE 10

Evaluation of the Transport Rate of PF3 and PF4 Through CaCo-2 Monolayer

In order to evaluate the permeability of the diacetoxy and dimethoxy derivatives of phenol red, the CaCo-2 model was used.

The CaCo-2 system is based on the intestinal properties of the Caco-2 cells. These cells preserve the polarity that is seen in the intestinal wall—an apical brush border that faces the intestinal lumen and a basolateral side that faces the body. Cells are grown on membranes, and form a tight monolayer (width of one cell, as in the intestine) allowing specific compounds to penetrate. Generally, large compounds do not penetrate the cells monolayer, whereby small compounds might penetrate, either via a hydrophilic route between the cells (termed paracellular permeability) or via a hydrophobic route (termed transcellular permeability). Known compounds serve as standards in this system: the hydrophilic Mannitol passes between the cells and the hydrophobic Propranolol passes through the cells. A schematic illustration of the CaCo-2 system is presented in FIG. 11.

Materials:
PF3 and PF4 were provided as dry powder. Prior to the assay the compounds were dissolved in DMSO and diluted in water to provide a stock solution of 0.5 mM (2.5% DMSO) and were kept protected from light until usage.

[$^3$H]-Mannitol Standard solution was prepared by diluting 26.3 Ci/mmol [3H]-Mannitol stock solution to 5.26 Ci/mmol final concentration in apical buffer (containing 25 mM D-glucose, 20 mM MES biological buffer, 1.25 mM CaCl2, 0.5 mM MgCl2, adjusted to pH 6.5 with KOH).

Propranolol Standard solution was prepared by diluting a 5 mM stock solution to 1 mM final concentration in apical buffer.

Caco-2 cells, originating from a human colorectal carcinoma, were provided by ATCC (American Type Culture Collection) at passage 47. Cells at passage 68 were used in these studies. Caco-2 cells were grown in high D-glucose DMEM medium supplemented with 1% L-glutamine, 1% nonessential amino acids, 1% sodium pyruvate, 1% penicillinstreptomycin and 10% fetal bovine serum.

Methods:
Cell Cultures: Caco-2 cells were cultured in 75 $cm^2$ culture flasks. The flasks were kept at 37° C. in an atmosphere of 5% $CO_2$ and 100% humidity. The culture medium was replaced every other day and the day before the experiment. For subculturing, the medium was removed and the cells were detached from the culture flasks with 0.25% Trypsin-EDTA. Culture medium with fetal bovine serum (FBS) was added to stop trypsinization.

Cells (passage 68) were harvested after 95% confluence and seeded at a density of 85,000 cells per polycarbonate membranes (0.4 μm pore size and a surface area of 0.33 $cm^2$) inserts. Cells on inserts were cultured for 10 days.

Confluence and differentiation of the cell monolayer on inserts was measured by the evaluation of the Trans-Epithelial-Electrical-Resistance (TEER). At the onset of experiments average TEER values were 613±25 ohms/$cm^2$.

Transport studies: Test substances transport across Caco-2 monolayers was investigated in 'apical to basolateral' direction (n=2), at two time points (45 and 90 minutes).

Prior to the experiment, the culture medium was removed; cells were washed twice with 150 μl apical buffer and 600 μl basolateral buffer (containing 25 mM D-glucose, 20 mM HEPES biological buffer, 1.25 mM $CaCl_2$, 0.5 mM $MgCl_2$, adjusted to pH 7.4 with KOH) and were incubated for 30 minutes at 37° C., 45 RPM, with the same buffers. At time 0, 30 μl buffer were removed from the apical chamber and 5-fold concentrated stock solutions of PF3 or PF4 were loaded.

Transport studies were performed at 37° C., with shaking at 45 RPM with either the tested compounds or standards (n=2). At each time point, aliquot of 120 μl Basolateral sample was drawn from each insert. For the radioactive marker Mannitol, 20 μl duplicate aliquots were drawn at each time point. The basolateral chamber volume was corrected to 600 μl after the first time point (45 minutes). At endpoint (90 minutes), the whole volume of the apical and basolateral chambers was collected.

Data Recording: Substance samples and propranolol standard samples were analyzed using HPLC (see below for analyses details). [$^3$H]-Mannitol samples were subjected to analysis by liquid scintillation counting in a Packard Top-Count NXT. The results were obtained in CPM.

LDH Assay: 100 μl of cells supernatant were removed from the basolateral chamber at the end of transport experiment. LDH release was assayed according to the manufacturer instructions using cytotoxicity detection kit (Roche, Cat. No. 1 644 793).

Cell recovery: At the end of the experiment, basolateral and apical buffers were replaced by growth medium. Inserts were incubated for additional 24 hours and TEER values were recorded the next day. Inserts with TEER values higher than 200 ohms/cm were considered as recovered.

Papp Calculations: Apparent permeability coefficients (Papp) of tested compounds and standards were calculated from the following equation:

$$Papp(t) = (C_t V/t) \times (1/C_0 A)$$

where $C_0$ is the initial concentration (at t=0) of the compound on the donor (apical side); $C_t$ is the concentration at the calculated time point (t) in the receiver (basolateral) chamber; V is receiver chamber volume; A is the surface area of the monolayer; and t is the elapsed time.

Compound and standards Recovery: At the last time point of the experiment (90 minutes), basolateral and apical amounts values were measured and recovery (%) of the tested compound or standard was calculated according to the following equation:

$$\text{Recovery \%} = (C_{90\,min} \times V_{basolateral}) + (C_{90\,min} \times V_{apical}) / C_0 \times V_{apical}$$

HPLC analyses: HPLC analyses were performed using a Waters 2790 HPLC system, equipped with PDA 996 detector (Waters). Analyses of PF3 and PF4 were performed using a Luna Phenyl-1-Hexyl 250-4.6 column, having particle size of 5 μm (Phenomenex, Cat No. 00G-4257-EO), operated at 40° C. A gradient solvent system of water (A) and acetonitrile (B) was used as a mobile phase, as follows:

| Time (minutes) | A (%) | B (%) |
|---|---|---|
| 1 | 95 | 5 |
| 20 | 5 | 95 |
| 22 | 95 | 5 |

Retentions time of PF3 was about 9.2; retention of PF4 was about 9.4.

Analyses of propranolol were performed using Waters ODS-2 column (Spherisorb® 150 mm, 4.6 mm internal diameter, 3 μm particles diameter) at 35° C. A gradient solvent system of 0.1% TFA (A) and acetonitrile containing 0.15 TFA (B) was used as a mobile phase, at 1 ml/minute flow rate, as follows:

| Time (minutes) | A (%) | B (%) |
|---|---|---|
| 15 | 50 | 50 |
| 20 | 5 | 95 |
| 25 | 5 | 95 |
| 26 | 95 | 5 |

Retention time of propranolol was about 17.3.

The data was processed using Millennium software. Processing wavelength was set to 200 nm. The sample amount was calculated using derived calibration curves.

Results:

CaCo-2 Transport:

Following transport experiments, and as a prerequisite for any transport analysis, Caco-2 monolayers are assayed in two viability assays. Short term damage to cell membrane is examined using LDH release assay, and long term damage is measured by recovery of transepithelial electrical resistance (TEER) values.

Specifically, an increase in the amount of dead or plasma membrane-damaged cells results in release of lactate dehydrogenase (LDH) enzyme to the surrounding buffer. The enzymatic activity of LDH is measured in a colorimetric assay. A surfactant that damages cell membranes is used as a positive control. Monolayers are considered recovered if TEER values are higher than 200 ohms/cm.

Short term damage—LDH Release: LDH activity in basolateral buffer from inserts of each group (n=2) was measured in a colorimetric assay as described hereinabove. Results are expressed as Mean±SD optical density (OD) values at 492 nm and are presented in FIG. 12. The positive control glycocholate was previously assayed and is shown for comparison.

As can be seen in FIG. 12, the cytotoxicity of PF4 was negligible. An increase in LDH activity was detected for PF3 at 0.1 mM, yet, for only one of the inserts and was not repeated, and was therefore attributed to a factor other than the tested PF3 compound.

Long Term Damage—Monolayer Recovery: The data obtained for the CaCo-2 monolayer recovery are presented in FIG. 13. TEER values were measured before (pre-assay) and 24 hours after transport experiment (post-assay) in all the inserts. Only the non-radioactive marker propranolol was measured. Results are expressed as Mean TEER values (ohms/cm)±SD. The horizontal line represents recovery threshold.

As can be seen in FIG. 13, TEER values of all tested groups showed that monolayers have recovered at the end of the experiment (values are≧200 ohms/cm). These results indicate that the tested substances did not cause monolayer damage, allowing the evaluation of 3PF and 4PF transport.

PF3 transport: The transport of PF3, at 0.1 mM and 0.02 mM concentrations, was evaluated using the protocol described hereinabove. 0.2 mM and 1 mM 3PF, $^3$H-mannitol and propranolol (n=2) standards were assayed in parallel. Samples from receiver chamber were removed at 45 and 90 minutes and analyzed in HPLC or counted with beta-scintillation counter.

FIG. 14 presents the Papp values of PF3, as compared to Papp standards values (of mannitol and propranolol). The data represent Papp mean values±standard deviation. As can be seen in FIG. 14, permeability standards displayed the expected values and allowed wide permeability grading.

The results obtained for PF3 show it was not detected at the lower concentration (0.02 mM) in the basolateral chamber during the assay. The fact that 3PF transport was detected for the higher concentration (0.1 mM) may indicate that low concentrations are undetectable by the practiced HPLC analysis.

The calculated Papp values of PF3 remained at the same order of magnitude along experimental time and were found to be higher than mannitol (a marker of paracellular transport) Papp values and lower than propranolol (a marker of transcellular transport) for both tested concentrations. These results indicate that PF3 permeability is in the low-medium range.

The calculated 3PF recovery values at experiment end point (90 minutes) were 53%±5% for the 1 mM concentration. The recovery of the 0.2 mM had a significant SD and is not presented. The relatively low concentration of 3PF at the apical and basolateral chambers at the experiment endpoint reveals high standard deviation, which is a basic feature in the Caco-2 model.

HPLC analyses showed the appearance of new peaks, retained at 7.7 and 8.2 minutes (data not shown), which were detected in the apical chamber at the endpoint. These peaks are presumably attributed to degradation products (e.g., phenol red) and may account for the low recovery.

The obtained results may further suggest that PF3 transport includes active transport, for example through PEPT1 pump.

Overall, the observation that 3PF is capable of crossing Caco-2 in a physiological permeability, and that it may further decompose in a physiological environment to phenol red, renders it a promising orally administered prodrug.

4PF transport: PF4 was not detected at the basolateral chamber for both tested concentrations.

The calculated PF4 recovery values at experiment end point (90 minutes) were 123%±48% and 105%±31% for the 1 mM and 0.2 mM, respectively.

EXAMPLE 11

Oral and Intravenous Pre-Formulations of PF3

In view of the advantageous higher permeability of PF3 in the CaCo-2 model experiments described in Example 10 above, further studies were conducted in order to develop vehicles of PF3 compatible with intravenous (I.V.) and/or oral administration or conscious animals Prior to the experiments, PF3 was kept at 2-8 °C. Solubility studied consisted of the solubility screening of PF3 against various compositions of co-solvents, utilizing a levigation approach (starting from 1 mg). Solubility was defined by the formation of a clear solution. Further, a compatible vehicle was evaluated for its maximal capacity. Compatible vehicles were incubated and observed for homogeneity and uniformity at several time points up to 24 hours at room temperature.

Intravenous administration pre-formulations: Various vehicle groups were tested, as follows:

As organic co-solvents compositions several combinations of DMA with PEG400 and saline were used. To obtain a saturated solution, PF3 was first dissolved in the minimal volume of DMA. PEG400 and saline were then added sequentially.

As inclusion complex vehicles, cyclodextrins (CD's) were used to bind PF3 within their cavity, through hydrophobic interactions, in order to increase the solubility of the PF3 in water. The degree of clarity of the solution was used to estimate the degree of the CD's encapsulation of the PF3.

As micro/nano emulsion vehicles, alcohol, oil, surfactants and water were combined with the PF3. First, the PF3 was suspended in minimal volume of alcohol. Then, oils and surfactants were added while vortexing. Finally, water was added to create a water-in-oil or oil-in-water emulsion, as a function of the different oil:water ratios tested. The emulsions were observed for precipitation.

Basic aqueous solutions were prepared by dissolving PF3 in a number of different basic aqueous solutions. Firstly, the PF3 was dissolved in DMA to maximal concentration about 100 mg/ml and then the various aqueous solutions were added. The solutions were titrated to achieve a suitable pH for IV administration (lower than 8).

A counter-ion salt solutions of PF3 was tested for solubility in water. PF3 was dissolved in a solution of 1% acetic acid in water, to a final concentration of 1 mg/ml. The solution became purple clear after short-term incubation in room temperature (5-10 minutes). After lyophilization, the counter-ion solubility in water was examined.

One mg of PF3 was dissolved in 50 µl of the tested vehicle to form a 20 mg/ml solution. This concentration is rated "sparingly soluble" by British Pharmacopoeia, 1993 (BP 93), and was therefore a suitable concentration for the required I.V. dosage. A grainy/turbid solution indicated a poor solubility and led to further dilution of the solution until it was clear. Additional dilutions were performed until the compound was fully dissolved, down to a minimal concentration level of 0.1 mg/ml, this level being rated "very slightly soluble" by BP 93 (supra).

The obtained results indicated that not all vehicle groups tested here could dissolve the PF3. PF3 was found to be sparingly soluble in DMA, reaching approximately 100 mg/ml. Since the amount of DMA allowed to be administrated to animals is limited, and in order to minimize the DMA content in the pre-formulation, several experiments were carried out examining various ratios of DMA:PEG400:saline.

Cyclodextrins (inclusion complexes) could only partly dissolve PF3. Using different cyclodextrins: PF3 ratios had no effect on the solubility of the PF3.

PF3 dissolved poorly in the emulsions tested, rendering these vehicles inapplicable for an IV pre-formulation.

Dissolving PF3 in a strong base (sodium hydroxide solution) resulted in a clear purple solution. Titration with acid to a pH more suitable for I.V. administration (lower than 8) resulted in immediate precipitation.

These studies therefore indicate that a preferred pre-formulation suitable for I.V. administration consists of 25% DMA, 40% PEG400 and 35% saline. In this pre-formulation PF3 was dissolved to a final concentration of 6.25 mg/ml. This DMA/PEG400/saline pre-formulation is stable for 45 minutes. This pre-formulation is limited to 3 mg/kg.

Oral administration pre-formulations: For the pre-formulation study 1-3 mg aliquots of PF3 were used. Two types of pre-formulations were tested as oral pre-formulations: (a) homogenization with detergents and (b) oil suspension. In (a), PF3 was dissolved in 0.45% CMC and 0.11% TWEEN80, and then homogenized for 5 minutes in two intervals until homogeneity was observed. In (b), PF3 was suspended in corn oil and was subjected to sonication for 1-2 hours at 60 °C. The vial was vortexed every 30 minutes and at the end of the procedure was observed for homogeneity.

The obtained results indicated that PF3 is only slightly soluble in 0.45% CMC/0.11% TWEEN80 vehicle and is practically insoluble in the corn oil vehicle.

These results indicate that the DMA/PEG400/Saline pre-formulation is also a preferred pre-formulation for oral administration. A CMC/TWEEN80 formulation, however, is also applicable.

EXAMPLE 12

Pharmacokinetic Studies of PF3 in Mice

While permeability studies have suggested that PF3 acts as a prodrug, producing phenol red upon removal of its acetate groups (see, Example 10 hereinabove), preliminary studies were conducted in mice, in order to obtain basic pharmacokinetic parameters following intravenous (I.V.) and oral (P.O.) administrations.

Materials and Methods:

PF3 was kept at 2-8° C., in dark, until used.

Male mice (ICR), 5 weeks of age, weighing 27-32 grams at study initiation were used. A total of sixteen animals were tested in each set of experiments, divided to 8 groups, 2 animals in each group. Animals were acclimatized for 5-7 days. All test animals was kept under environmental controlled housing conditions throughout the entire study period, and maintained in accordance with Harlan Biotech Israel (HBI) approved standard operation procedures (SOP's).

Intravenous (I.V.) administration: Intravenous administration of PF3 was done at a dose of .25 mg/kg (4 ml/kg volume dosage). A single slow intravenous injection (over a period of approximately one minute) was administered into one of the tail veins of each animal.

Dosing solutions were prepared in a co-solvent vehicle system containing DMA:PEG400:Saline 25:40:35 respectively (e.g., each 1 ml consists of 0.25 ml DMA, 0.4ml PEG400 and 0.35 ml Saline).

The final concentration of each dosing solution was 6.25 mg/ml. In view of the limited solubility (30 minutes) of PF3 in the vehicle, the compound was initially dissolved in DMA and PEG 400 to achieve a concentration of 9.61 mg/ml. Prior to each dosing session, saline was added drop by drop at the necessary amount while mixing on vortex (e.g., to prepare 0.5 ml of dosing solution, 175 µl of saline was added to 325 µl of 9.61 mg/ml of the PF3 in DMA and PEG 400). Dosing solutions were freshly and identically prepared prior to dosing, as deemed necessary. In all cases dosing time did not exceed the 30 minutes from the addition of saline to the DMA-PEG 400 solution.

Blood samples were taken at the following time points: pre-dosing (time 0), 5, 15, 30, 60, 90, 120 and 300 minutes post dosing, two animals per time point, by retro orbital sinus bleeding under $CO_2$ anesthesia. Individual blood samples of at least 0.4 ml whole blood were collected into pre-labeled lithium heparin coated tubes. Plasma separation was made as soon as possible after collection, by centrifugation at 2500G for 15 minutes. After centrifugation supernatant was transferred to eppendorff tube (1.5 ml) pre-labeled with the appropriate animal number, study number and time post dosing. Plasma samples were kept at about −20° C.

Oral (P.O.) administration: P.O. administration of PF3 was done at a dose of 62.5 mg/kg (volume dosage of 10 ml/kg). Administration to test animals was performed orally, following food deprivation of about 3.5-5 hours, by the use of gavage needle made of stainless steel which was introduced directly to the stomach.

The final concentration of each dosing solution was 6.25 mg/ml. Dosing solutions were prepared as described hereinabove for the I.V. administration.

Blood samples were taken, as described hereinabove, at the following time points: 30, 45, 60, 120, 180, 240, 300 and 360 minutes post dosing, two animals per time point, by retro orbital sinus bleeding under $CO_2$ anesthesia.

Samples Analysis: Plasma samples were analyzed both for PF3 (phenol red diacetate) presence and phenol red presence. Analysis was performed in Analyst Ltd., using LC/MS/MS method.

The chromatographic separation was achieved on a Gemini C1 8 column (50×2.0 mm, 5 µm), using 50:50 acetonitrile: water solution containing 0.1% $NH_4OH$ as the mobile phase, at a flow rate of 0.3 ml/minute. Retention times: Phenol red—about 0.4 minutes; PF3—about 3.5 minutes.

All samples were analyzed by the Micromass Quattro Pt triple-quadrupole mass selective detector equipped with an electrospray ionization source. Negative ionization mode was used for phenol red and positive ionization mode was used for PF3. The system includes a 2795 HT Waters HPLC and Masslynx v.4.0 software. Quanlynx v.4.0 software was used for calculation.

For calculation of phenol red concentration in samples, weighted linear regression curves ($1/x^2$) were calculated from response of analyte versus calibration standard concentration. The weighted linear regression correlation coefficient was grater than 0.99.

Quantitation limit (QL) of phenol red was defined as the lowest concentration of the calibration curve: 25 ng/ml. The signal to noise ratio of the QL sample (25 ng/ml) was 10.8.

Quantitation limit of phenol red acetate was defined as the lowest concentration of the calibration curve: 2.5 ng/ml. The signal to noise ratio of the QL sample (2.5 ng/ml) was 25.4.

All standards, when back-calculated, fell within ±15% of theoretical values.

Phenol red was determined in plasma over the concentration range 25-2000 ng/ml (nominal concentration) and PF3 over the concentration range 2.5-1000 ng/ml by HPLC-MS/MS.

K Parameters Calculations: PK parameters were calculated using Winnonlin Pro 4.01 software (Pharsight).

Results:

Intravenous Administration:

Sample Analysis: The results obtained by sample analysis are presented in Table 1 below.

TABLE 1

| Animal No. | Time post dosing (minutes) | PF3 Concentration* (µg/ml) | Phenol red Concentration (µg/ml) | |
|---|---|---|---|---|
| | | | Analyzed | Estimated** |
| 15 | Pre-Dosing | n/d | 0.03 | |
| 16 | Pre-Dosing | n/d | 0.02 | |
| 4 | 5 | n/d | >20 | 67 |
| 17 | 5 | n/d | >20 | 43 |
| 5 | 15 | n/d | >20 | 45 |
| 19 | 15 | n/d | >20 | 34 |
| 7 | 30 | n/d | >20 | 20 |
| 8 | 30 | n/d | >20 | 52 |
| 9 | 60 | n/d | 4.12 | |
| 10 | 60 | n/d | 4.33 | |
| 11 | 90 | n/d | 4.58 | |
| 12 | 90 | n/d | 2.19 | |
| 13 | 125 | n/d | 0.76 | |
| 1 | 300 | n/d | 0.22 | |
| 2 | 300 | n/d | 0.29 | |

*n/d = not detected and denotes a concentration lower than 5 ng/ml
**Phenol red concentrations higher than the upper limit of the calibration curve (20 µg/ml) were estimated.

As can be seen in Table 1, following I.V. administration, the pro-drug PF3 was not observed even after 5 minutes. On the other hand, phenol red drug is present in relatively high concentrations. Phenol red pre-dosing values are considered negligible (within the lowest limit of its calibration curve).

Pharmacokinetic Parameters: For pharmacokinetic (PK) parameters calculations, phenol red plasma profile was plotted, and is presented in FIG. 15.

Table 2 below presents the PK parameters following I.V. administration of PF3.

TABLE 2

| PK Parameter | Unit | Value |
|---|---|---|
| Half Life | min | 40 |
| AUC (area under the curve) | min × µg/ml | 2232 |
| Clearance | ml/min/kg | 11 |
| MRT (mean residence time) | min | 32 |
| Volume of distribution (Vss) | ml/kg | 367 |

Oral Administration:

Samples Analysis: The results obtained by samples analysis are presented in Table 3 below.

TABLE 3

| Animal No. | Time post dosing (minutes) | PF3 Concentration* (µg/ml) | Phenol red Concentration (µg/ml) |
|---|---|---|---|
| 2 | 30 | n/d | 5.59 |
| 3 | 45 | n/d | 2.86 |
| 4 | 45 | n/d | 2.67 |
| 5 | 60 | n/d | 11.17 |
| 6 | 60 | n/d | 4.21 |
| 7 | 123 | n/d | 1.46 |
| 8 | 122 | n/d | 6.12 |
| 9 | 180 | n/d | 0.24 |
| 10 | 180 | n/d | 0.12 |
| 11 | 240 | n/d | 0.08 |
| 12 | 241 | n/d | 0.11 |
| 13 | 300 | n/d | 6.61 |

TABLE 3-continued

| Animal No. | Time post dosing (minutes) | PF3 Concentration* (µg/ml) | Phenol red Concentration (µg/ml) |
|---|---|---|---|
| 14 | 300 | n/d | 0.2 |
| 15 | 360 | n/d | 0.13 |
| 16 | 362 | n/d | 0.14 |

*n/d = not detected and denotes a concentration lower than 5 ng/ml

As can be seen in Table 3, PF3 pro-drug is clearly absorbed in the intestine. The pro-drug PF3 is not detected in the plasma while phenol red drug is present in fairly high concentrations, even after 6 hours post-dosing.

Pharmacokinetic Parameters: For pharmacokinetic (PK) parameters calculations, phenol red plasma profile was plotted, and is presented in FIG. 16.

Table 4 below presents the PK parameters following P.O. administration of PF3.

TABLE 4

| PK Parameter | Unit | Value |
|---|---|---|
| Half Life | min | 32 |
| AUC | min × µg/ml | 904 |
| MRT | min | 131 |
| F, Bioavailability | % | 16 |

As can be seen in FIG. 16 and Table 4, the obtained data is relatively variable, presumably due to experimental limitations, such as choice of species (mice) and low number of animals per time point (n=2). Nevertheless, basic and preliminary PK parameters such as half life ($t_{1/2}$), volume of distribution, clearance and bioavailability were determined.

PK parameters of PF3 indicate that the drug is absorbed in the intestine with 16% bioavailability, thus demonstrating the beneficial use of phenol red derivatives as therapeutically active agents.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating pancreatic islet amyloid plaque associated with type II diabetes mellitus in a subject in need thereof, said pancreatic islet amyloid plaque exhibiting cytotoxicity towards pancreatic β cells, the method comprising orally administering to the subject, a therapeutically effective amount of pyrocetechol violet or a pharmaceutically acceptable salt thereof.

2. The method of claim 1, wherein said administering is effected at a concentration of said compound not exceeding 4 mg/Kg body weight/hour.

* * * * *